US012213962B2

(12) United States Patent
Spencer et al.

(10) Patent No.: US 12,213,962 B2
(45) Date of Patent: Feb. 4, 2025

(54) DRUG RESISTANT IMMUNOTHERAPY FOR TREATMENT OF A CANCER

(71) Applicants: Emory University, Atlanta, GA (US); The UAB Research Foundation, Birmingham, AL (US); Children's Healthcare of Atlanta, Inc., Atlanta, GA (US)

(72) Inventors: Harold Trent Spencer, Marietta, GA (US); Anindya Dasgupta, Anderson, SC (US); Lawrence S. Lamb, Birmingham, AL (US)

(73) Assignees: Emory University, Atlanta, GA (US); The UAB Research Foundation, Birmingham, AL (US); Children's Healthcare of Atlanta, Inc., Atlanta, GA (US)

( * ) Notice: Subject to any disclaimer, the term of this patent is extended or adjusted under 35 U.S.C. 154(b) by 486 days.

(21) Appl. No.: 16/708,180

(22) Filed: Dec. 9, 2019

(65) Prior Publication Data
US 2020/0323903 A1    Oct. 15, 2020

Related U.S. Application Data

(63) Continuation of application No. 16/283,669, filed on Feb. 22, 2019, now Pat. No. 10,543,233, which is a continuation of application No. 14/283,478, filed on May 21, 2014, now Pat. No. 10,322,145, which is a continuation of application No. 13/505,098, filed as application No. PCT/US2010/054608 on Oct. 29, 2010, now abandoned.

(60) Provisional application No. 61/257,136, filed on Nov. 2, 2009.

(51) Int. Cl.
| A61K 35/17 | (2015.01) |
| A61K 31/4188 | (2006.01) |
| A61K 31/495 | (2006.01) |
| A61K 31/519 | (2006.01) |
| A61K 39/00 | (2006.01) |
| C12N 5/0783 | (2010.01) |
| A61K 35/12 | (2015.01) |

(52) U.S. Cl.
CPC ........ *A61K 31/4188* (2013.01); *A61K 31/495* (2013.01); *A61K 31/519* (2013.01); *A61K 39/4611* (2023.05); *A61K 39/4613* (2023.05); *A61K 39/4644* (2023.05); *C12N 5/0636* (2013.01); *C12N 5/0638* (2013.01); *A61K 35/12* (2013.01); *A61K 2035/124* (2013.01); *A61K 2239/48* (2023.05); *C12N 2510/00* (2013.01)

(58) Field of Classification Search
CPC ...................................................... A61K 35/17
See application file for complete search history.

(56) References Cited

U.S. PATENT DOCUMENTS

| 6,071,512 | A | 6/2000 | Kriegler |
| 7,078,034 | B2 | 7/2006 | Lamb |
| 2006/0115481 | A1* | 6/2006 | Lindhofer .......... C07K 16/3053 424/155.1 |
| 2012/0258531 | A1 | 10/2012 | Spencer et al. |
| 2020/0188436 | A1 | 6/2020 | Ho, Jr. et al. |
| 2021/0322475 | A1 | 10/2021 | Lam, Jr. et al. |

FOREIGN PATENT DOCUMENTS

| WO | WO 1997/32025 | 9/1997 |
| WO | WO 2014/164554 A1 | 10/2014 |
| WO | WO 2015/120363 A1 | 8/2015 |
| WO | WO 2017/041106 | 3/2017 |

OTHER PUBLICATIONS

McMillin et al. (2004, Molecular Therapy, vol. 9, S97-S98, Abstract No. 253) (Year: 2004).*
Tran et al. (1995, J. Immunology, vol. 155, pp. 1000-1009) (Year: 1995).*
McMillin et al. (2006, Human Gene Therapy, vol. 17, pp. 798-806) (Year: 2006).*
Ullrich et al. (2008, Cell Death and Diff., vol. 15, pp. 21-28) (Year: 2008).*
Milsom et al. (2008, Cancer Research, vol. 68(15), pp. 6171-6180) (Year: 2008).*
Imai et al. (2005, Blood, vol. 108(1), pp. 376-383) (Year: 2005).*
Adair et al., "Gene therapy enhances chemotherapy tolerance and efficacy in glioblastoma patients," *Journal of Clinical Investigation* 124(9): 4082-4092 (Sep. 2014).
Bardenheuer et al., "Resistance to cytarabine and gemcitabine and in vitro selection of transduced cells after retroviral expression of cytidine deaminase in human hematopoietic progenitor cells," *Leukemia* 19: 2281-2288 (2005).
Beard et al., "Efficient and stable MGMT-mediated selection of long-term repopulating stem cells in nonhuman primates," *Journal of Clinical Investigation* 120(7): 2345-2354 (Jul. 2010).

(Continued)

*Primary Examiner* — Anoop K Singh
*Assistant Examiner* — David A Montanari
(74) *Attorney, Agent, or Firm* — Klarquist Sparkman, LLP; Susan Alpert Siegel; Gregory K. Scott

(57) ABSTRACT

The present disclosure is generally related to methods for combining chemotherapy and immunotherapy for the treatment of a cancer. The methods also relate to generating a drug-resistant cytotoxic immune cell line and uses thereof in conjunction with cytotoxic drugs

14 Claims, 24 Drawing Sheets

Specification includes a Sequence Listing.

(56) References Cited

OTHER PUBLICATIONS

Bryant et al., "Characterization and immunotherapeutic potential of γδ T-cells in patients with glioblastoma," *Neuro-Oncology* 11: 357-367 (Feb. 11, 2009).
Cesano et al., "TALL-104 Cell Therapy of human solid tumors implanted in immunodeficient (SCID) mice," *Anticancer Research* 18: 2289-2296 (1998).
Chamberlain, "Treatment options for glioblastoma," *Neurosurg Focus* 20(4): E19, pp. 1-9, (Apr. 15, 2006).
Chinnasamy et al., "Lentivirus-mediated expression of mutant MGMT (P140k) protects human CD34+ cells against the combined toxicity of O6-benzylguanine and 1,3-Bis(2-Chloroethyl)-nitrosourea or temozolomide," *Human Gene Therapy* 15: 758-769 (2004).
Dasgupta et al., "Engineered drug-resistant immunocompetent cells enhance tumor cell killing during a chemotherapy challenge," *Biochemical and Biophysical Research Communications* 391: 170-175 (2010).
Dasgupta et al., "Treatment of a solid tumor using engineered drug-resistant immunocompetent cells and cytotoxic chemotherapy," *Human Gene Therapy* 2012 23: 711-721 (Jul. 2012).
Dotti et al., "Review: Current status of genetic modification of T Cells for cancer treatment," *Cytotherapy* 7(2): 262-272 (2005).
Engelhardt, "Molecular mechanisms involved in T Cell migration across the blood-brain barrier," *J. Neural Transm.* 113(4): 477-485 (Apr. 2006).
Extended European Search Report for EP Application No. 10827507.4 (dated Aug. 19, 2013).
Friedman et al., "Temozolomide and treatment of malignant glioma," *Clinical Cancer Res.* 6(7): 2585-2597(Jul. 2000).
Gangadharan et al. "High-level expression of porcine factor VIII from genetically modified bone marrow-derived stem cells," *Blood* 107: 3859-3864 (2006).
Geoerger et al., "Antitumor activity of a human cytotoxic T-Cell line (TALL-104) in brain tumor xenografts," *Neuro-Oncology* 103-113 (2000).
Gerull et al., "In Vivo selection and chemoprotection after drug resistance gene therapy in a nonmyeloablative allogeneic transplantation setting in dogs," *Human Gene Therapy* 18: 451-456 (2007).
Gong et al., "Characterization of a human cell line (NK-92) with phenotypical and functional characteristics of activated natural killer cells," *Leukemia* 8(4): 652-658 (1994).
Grossman et al., "Immunosuppression in patients with high grade gliomas treated with radiation and temozolomide," *Clin. Cancer Res.* 17(16): 5473-5480 (Aug. 15, 2011).
Heimberger et al., "Immunological responses in a patient with glioblastoma multiforme treated with sequential courses of temozolomide and immunotherapy: Case study," *Neuro-Oncology* 10: 98-103 (2008).
Hermans et al., "Synergistic effect of metronomic dosing of cyclophosphamide combined with specific antitumor immunotherapy in a murine melanoma model," *Cancer Res* 63: 8408-8413 (2003).
Jiang et al., "Treatment of advance gastric cancer by chemotherapy combined with autologous cytokine-induced ciller cells," *Anticancer Research* 26: 2237-2242 (2006).
Kershaw et al., "Supernatural T Cells: genetic modification of T Cells for cancer therapy," *Nature Reviews* 5: 928-940 (Dec. 2005).
Kono et al., "Prognostic significance of adoptive immunotherapy with tumor associated lymphocytes in patient with advanced gastric cancer: a randomized trial," *Clinical Cancer Research* 8: 1767-1771 (Jun. 2002).
Kushman et al., "Expression of human glutathione S-transferase P1 confers resistance to benzo[a]pyrene or benzo[a pyrene-7,8-dihydrodiol mutagenesis, macromolecular alkylation and formation of stable N2-Gua-BPDE adducts in stably transfected V79MZ cells co-expressing hCYP1A1," *Carcinogenesis*, 28(1): 207-214 (2007).
Lamb and Lopez, "γδ T Cells: A new frontier for immunotherapy?" Biology of Blood and Marrow Transplantation 11: 161-168 (2005).
Lamb et al., "Engineered drug resistant γδ T Cells kill glioblastoma cell lines during a chemotherapy challenge: A strategy for combining chemo- and immunotherapy," *PLoS ONE* 8(1): e51805, 9 pages (Jan. 2013).
Lamb et al., "γδ T Cells as immune effectors against high-grade gliomas," *Immunol.* Res. 45: 85-95 (2009).
Lamb et al., "γδ T Cells: a new frontier for immunotherapy?," *Biology of Blood Marrow Transplantation* 11: 161-168 (Mar. 2005).
Larochelle et al., "In vivo selection of hematopoietic progenitor cells and temozolomide dose intensification in rhesus macaques through lentiviral transduction with a drug resistance gene," *J. Clin. Invest.* 119: 1952-1963 (2009).
Litterman et al., "Profound impairment of adaptive immune responses by alkylating chemotherapy," *J. Immunol.* 190(12): 6259-6268 (Jun. 15, 2013).
Mattarollo et al., "Chemotherapy and zoledromate sensitize solid tumour cells to Vγ9Vδ2 T Cell cytotoxicity," *Cancer Immunol Immunother* 56: 1285-1297 (2007).
Maze et al., "Retroviral-mediated expression of the P140A, but not P140A/G156A, mutant form of O6-methylguanine DNA methyltransferase protects hematopoietic cells against O6-benzylguanine sensitization to chloroethylnitrosourea treatment," *JPET* 290: 1467-1474 (1999).
McMillin et al., "Complete regression of large solid tumors using engineered drug resistance hematopoietic cells and anti CD-137 immunotherapy," *Human Gene Therapy* 17: 798-806 (2006).
McMillin et al., "Highly efficient transduction of repopulating bone marrow cells using rapidly concentrated polymer-complexed retrovirus," *Biochemical and Biophysical Research Communications* 330: 768-775 (2005).
McMillin et al., "Regression of large solid tumors using engineered drug resistant immunocompetent cells and selective chemotherapy," *Molecular Therapy* 9: S97-S98, (Abstract No. 253) (2004).
Milsom et al., "Reciprocal relationship between O6-methylguanine-DNA methyltransferase P140K expression level and chemoprotection of hematopoietic stem cells," *Cancer Research* 68(15): 6171-6180 (Aug. 1, 2008).
Mitchell et al., "Immunotherapy of malignant brain tumors," *Immunological Rev.*, 222: 70-100 (Apr. 2008).
Neff et al., "Polyclonal chemoprotection against temozolomide in a large-animal model of drug resistance gene therapy," *Blood* 105: 997-1002 (2005).
Nivens et al., "Engineered resistance to camptothecin and antifolates by retroviral coexpression of tyrosyl DNA phosphodiesterase-I and thymidylate synthase," *Cancer Chemother Pharmacol* 53: 107-115 (2004).
Nowak et al.., "Synergy between chemotherapy and immunotherapy in the treatment of established murine solid tumors.," *Cancer Res.* 63: 4490-4496 (2003).
Omuro et al., "Temozolomide and methotrexate for primary central nervous system lymphoma in the elderly," *J. Neurooncol.* 85(2): 207-211(Nov. 2007).
Parkhurst et al., "Characterization of genetically modified T-cell receptors that recognize the CEA:691-699 peptide in the context of HLA-A2.1 on human colorectal cancer cells," 2009, *Clin. Can. Res.*, 15(1): 169-180 (Jan. 1, 2009).
Pollok et al., "In Vivo Selection of Human Hematopoietic Cells in a Xenograft Model Using Combined Pharmacologic and Genetic Manipulations" Human Gene Therapy, 2003; 14: 1703-1714.
Porter et al., "Interfering RNA-mediated purine analog resistance for in vitro and in vivo cell selection," *Blood* 112: 4466-4474 (2008).
Ramakrishnan et al., "Combined modality immunotherapy and Chemotherapy: a new perspective," *Cancer Immunol Immunother* 57: 1523-1529 (2008).
Rosenberg et al., "Cancer regression in patients with metastatic melanoma after the transfer of autologous antitumor lymphocytes," *PNAS* 101(suppl. 2): 14639-14645 (Oct. 5, 2004).
Sadelain et al., "Targeting tumours with genetically enhanced T lymphocytes," *Nature Reviews* 3: 35-45 (Jan. 2003).
Sawai et al., "Protection and in vivo selection of hematopoietic stem cells using temozolomide, O6-benzylguanine, and an alkyltransferase-expressing retroviral vector," *Molecular Therapy* 3(1): 78-87 (Jan. 2003).

(56) References Cited

OTHER PUBLICATIONS

Schroeder et al., "Abstract: Forced expression of the "IY" mutant inosine monophosphate dehydrogenase II results in physiologically significant resistance to mycophenolic acid in vitro," *Blood* (American Society of Hematology Annual Meeting Abstracts) 108: Abstract 5480 (2006).

Spencer et al. "A Gene Transfer Strategy for making bone morrow cells resistance to Trimetrexate," *Blood* 87: 2579-2587 (1996).

Sugimoto et al. "Drug-selected co-expression of P-glycoprotein and gp91 in vivo from an MDR1-bicistronic retrovirus vector Ha-MDR-IRES-gp91," *J Gene Med* 5: 366-376 (2003).

Suzuki et al., "Enhancing effect of tumor necrosis factor (TNF)-α, but not IFN-gamma, on the tumor-specific cytotoxicity of γδ T Cells from glioblastoma patients," *Cancer Letters* 140: 161-167 (1999).

Sweeney et al., "Methotrexate exacerbates tumor progression in a murine model of chronic myeloid leukemia," *JPET* 300: 1075-1084 (2002).

Takebe et al., "Generation of dual resistance to 4-hydroperoxycyclophosphamide and methotrexate by retroviral transfer of the human aldehyde dehydrogenase class 1 gene and a mutated dihydrofolate reductase gene," *Molecular Therapy* 3(1): 88-96 (Jan. 2001).

Tam et al., "Immunotherapy of malignant melanoma in a SCID mouse model using the highly cytotoxic natural killer cell line NK-92," *Journal of Hematotherapy* 8: 281-290 (1999).

Van Tellingen et al., "Overcoming the blood-brain tumor barrier for effective glioblastoma treatment," *Drug Resistance Updates* 19: pp. 1-12 (Mar. 2015).

Vetter et al., "Loss of nonclassical MHC molecules MIC-A?B expression during progression of uveal melanoma," *British Journal of Cancer* 91:1495-1499 (2004).

Yan et al., "Antileukemia activity of a natural killer cell line against human leukemias," *Clin Cancer Res* 4: 2859-2868 (1998).

Zeilske et al., "In vivo selection of MGMT(P140K) lentivirus-transduced human NOD/SCID repopulating cells without pretransplant irradiation conditioning," *J. Clin. Invest.* 112: 1561-1570 (2003).

Hutt, D. Chapter 13: "Engraftment, Graft Failure, and Rejection." In: Kenyon et al. The European Blood and Marrow Transplantation Textbook for Nurses: Under the Auspices of EBMT. Springer, published on-line (Nov. 22, 2017).

McEntee, et al., "The former annotated human pseudogene dihydrofolate reductase-like 1 (DHFRL1) is expressed and functional," *Proc. Natl. Acad. Sci.*, vol. 108, No. 37, pp. 15157-15162 (Sep. 13, 2011).

McMillian et al., "Highly efficient transduction of repopulating bone marrow cells using rapidly concentrated polymer-complexed retrovirus," *Biochemical and Biophysical Research Communications* 330: 768-775, 2005.

Mohr, et al., "Efficient immunoaffinity chromatography of lymphocytes directly from whole blood," *Scientific Reports* 8:16731, 6 pages (published on-line Nov. 13, 2018).

\* cited by examiner

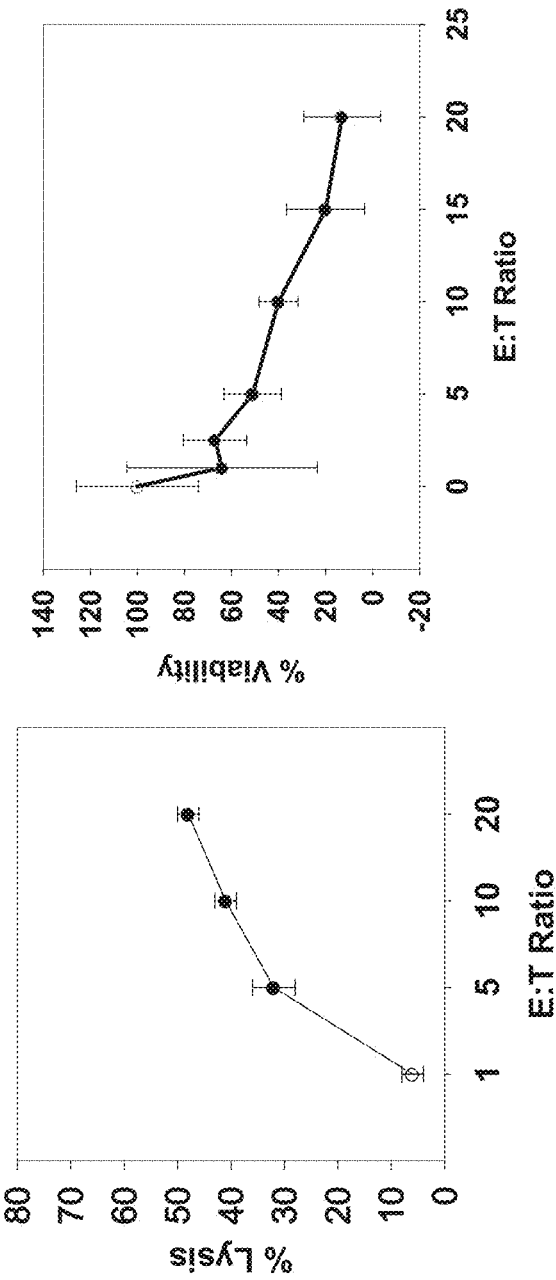
*Fig. 2B*
*Fig. 2A*
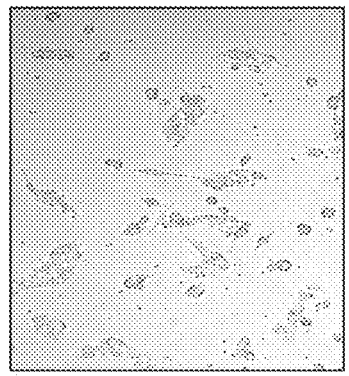
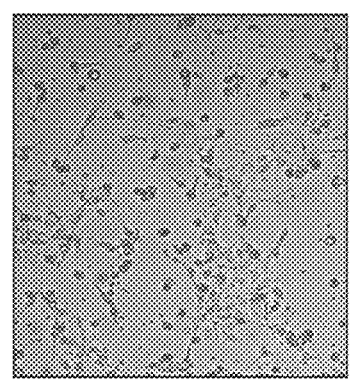
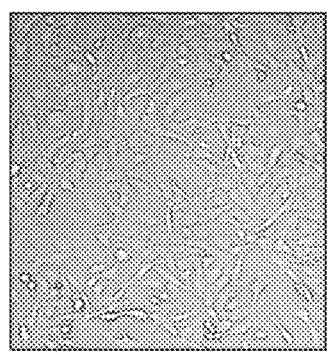
*Fig. 2C*

Saline injected control mice

γδ injected mice (5:1)

MGMT optimized codon sequence:
ATGGACAAAGATTGCGAGATGAAGCGGACCACACTGGACTCCCCCCTGGGCAAACTGGAGCTGTCTGGCTGTGAA
CAGGGGCTGCACGAGATCAAACTGCTGGGGACCAAAGGGCACTAGCGCCTGATGCTGTGTGAAGTGCCAGCTCCAGCT
GCTGTGCTGGGAGGACCTGAGCGTGCCTGATGCAGTGACCGCCTGGCTTACTTCCATCAGCCTGAAGCC
ATCGAGGAATTTCCCGTGCCCTGCCACTGCCACCATCCAGTGTTCCAGCAGGAGAGTTTACAAGGCAGGTGCTGTGG
AAGCTGCTGAAAGTGGTGGGGAGGAAGTTCGGGGAGCTATGAGAGGCAATCCAGTGAAAGATCCTGATTCCCTGCTGTGT
GCTGCTCGGGCCGTGTGGGGAACTATTCTGGGGAACTGGACTGGGAGGGTCTAGGGAGCTTGGCTGAAGGGAGCTACCTCAGGA
AGCCCACCTGCCGGCCGGAATTGA DHFR optimized codon sequence:
ATGGTGGGTCCCTGAACTGCATCGTGGCTGTGTCTCAGAACATGGGAATTGGCAAGAATGGGACTACCCCTTGG
CCCCCTCTGCGGAACGAGTTCAGATATTTTCAGAGGATGACCACAGAGAACCTAGCTCCGTGGAAGGAAACAGAACCTG
GTCATCATGGGAAAGAAAACTTGGTTCAGTATTCCCGAGAAGAACGCCCTCTGAAAGGACGGATCAATCTGGTG
CTGTCCCGAGAGAGCCAGGGCGACCACCCAAGTGGACATGTGTGGATTGTGGGCGGGTCTAGTGTGTAGAGGCGATGCTGAAGCTG
ACCGAGCAGCCCGAACTGGCCAACAAGTGGCCATGTGGACATGTGTGGATTGTGGGCGGGACTTTGAGAGCGATACATTCTTTCCC
ATGAATCACCCAGGTGTGTGTCGTGCTGCTGAAACTGCTCCTGAATATCCAGGCCGTGCTGCTGATGTGCAGGAGGAAAAGGGG
GAGATTGACCTGGAAAGTACAAATTCGAGGTGTATGAGAAGAACGATTGA

Fig. 28

SEQUENCE LISTING

<160> NUMBER OF SEQ ID NOS: 6

<210> SEQ ID NO 1
<211> LENGTH: 24
<212> TYPE: DNA
<213> ORGANISM: Homo sapiens

<400> SEQUENCE: 1
aaactggagc tgtctggctg tgaa            24

<210> SEQ ID NO 2
<211> LENGTH: 24
<212> TYPE: DNA
<213> ORGANISM: Homo sapiens

<400> SEQUENCE: 2

```
aaactctcct gctggaacac tgga                                            24

<210> SEQ ID NO 3
<211> LENGTH: 24
<212> TYPE: DNA
<213> ORGANISM: Homo sapiens

<400> SEQUENCE: 3
catgggaatt ggcaagaatg gcga                                            24

<210> SEQ ID NO 4
<211> LENGTH: 24
<212> TYPE: DNA
<213> ORGANISM: Homo sapiens

<400> SEQUENCE: 4
tgaccaggtt ctgtttccct tcca                                            24

<210> SEQ ID NO 5
<211> LENGTH: 624
<212> TYPE: DNA
<213> ORGANISM: Homo sapiens

<400> SEQUENCE: 5
atggacaaag attgcgagat gaagcggacc acactggact cccccctggg caaactggag     60
ctgtctggct gtgaacaggg gctgcacgag atcaaactgc tgggaaaggg cactagcgcc    120
gctgatgctg tggaagtgcc agctccagct gctgtgctgg aggacctga gccactgatg     180 cagtgcaccg cctggctgaa cgcttacttc catcagcctg aagccatcga ggaatttccc    240
gtgcctgccc tgcaccatcc agtgttccag caggagagtt ttacaaggca ggtgctgtgg    300
aagctgctga agtggtgaa gttcggggaa gtgatttcct accagcagct ggctgctctg     360
gctggaaacc caaaagctgc tcgggccgtg ggaggagcta tgagaggcaa tccagtgaag    420
atcctgattc cctgccacag ggtggtgtgt agctccggag ctgtggggaa ctattctggg    480
ggactggccg tgaaagaatg gctgctggct cacgagggac ataggctggg aaagcctggc    540
ctgggagggt ctagtggact ggctggagct tggctgaagg gagctggagc tacctcagga    600
agcccacctg ccggccggaa ttga                                           624

<210> SEQ ID NO 6
<211> LENGTH: 564
<212> TYPE: DNA
<213> ORGANISM: Homo sapiens

<400> SEQUENCE: 6
atggtggggt ccctgaactg catcgtggct gtgtctcaga acatgggaat tggcaagaat     60
ggcgactacc cttggccccc tctgcggaac gagttcagat attttcagag gatgaccaca    120
actagctccg tggaagggaa acagaacctg gtcatcatgg gaaagaaaac ttggttcagt    180
attcccgaga agaaccgccc tctgaaagga cggatcaatc tggtgctgtc cagagagctg    240
aaggaaccac cccagggcgc ccactttctg tcaaggagcc tggacgatgc tctgaagctg    300
accgagcagc ccgaactggc caacaaagtg gacatggtgt ggattgtggg cgggtctagt    360
gtgtacaagg aggccatgaa tcacccaggc catctgaaac tgttcgtgac ccggatcatg    420
caggactttg agagcgatac attctttccc gagattgacc tggaaaagta caaactgctg    480
cctgaatatc caggcgtgct gtctgatgtg caggaggaaa aggggatcaa gtacaaattc    540
gaggtgtatg agaagaacga ttga                                           564
```

DRUG RESISTANT IMMUNOTHERAPY FOR TREATMENT OF A CANCER

CROSS REFERENCE TO RELATED APPLICATION

This is a continuation of U.S. patent application Ser. No. 16/283,669, filed Feb. 22, 2019, which is a continuation of U.S. patent application Ser. No. 14/283,478, filed on May 21, 2014, issued as U.S. Pat. No. 10,322,145, which is a continuation of U.S. application Ser. No. 13/505,098, filed Apr. 30, 2012, now abandoned, which is a 371 U.S.C. application of PCT Application No. PCT/US2010/054608, filed Oct. 29, 2009, which claims the benefit of U.S. provisional application No. 61/257,136, filed on Nov. 2, 2009. The prior applications are hereby incorporated by reference in their entirety.

STATEMENT OF GOVERNMENT SUPPORT

This invention was made with government support under NS057341, CA097247, and HL087969 awarded by the National Institutes of Health. The government has certain rights in the invention

TECHNICAL FIELD

The present disclosure is generally related to methods for combining chemotherapy and immunotherapy for the treatment of a cancer. The methods also relate to generating a drug-resistant cytotoxic immune cell line and uses thereof in conjunction with cytotoxic drugs.

BACKGROUND

Although outstanding progress has been made in the fields of cancer detection and tumor cell biology, the treatment of late-stage and metastatic cancer remains a major challenge. Cytotoxic chemotherapy agents remain among the most used and successfully employed anti-cancer treatments. However, they are not uniformly effective, and the introduction of these agents with novel therapies, such as immunotherapies, is problematic. For example, chemotherapy agents can be detrimental to the establishment of robust anti-tumor immunocompetent cells due to the agents' non-specific toxicity profiles. Small molecule-based therapies targeting cell proliferation pathways may also hamper the establishment of anti-tumor immunity. However, if chemotherapy regimens that are transiently effective can be combined with novel immunocompetent cell therapies then significant improvement in anti-neoplastic therapy might be achieved.

Several drug resistant genes have been identified that can potentially be used to confer drug resistance to targeted cells, and advances in gene therapy techniques have made it possible to test the feasibility of using these genes in drug resistance gene therapy studies (Sugimoto et al., (2003) J. Gene Med. 5: 366-376; Spencer et al., (1996) Blood 87: 2579-2587; Takebe et al., (2001) Mol. Ther. 3: 88-96; Kushman et al., (2007) Carcinogenesis. 28: 207-214; Nivens et al., (2004) Cancer Chemother. Pharmacol. 53: 107-115; Bardenheuer et al., (2005) Leukemia 19: 2281-2288; Zielske et al, (2003) J. Clin. Invest. 112: 1561-1570). For example, a shRNA strategy was used to decrease the levels of hypoxanthine-guanine phosphoribosyltransferase (HPRT), which conferred resistance to 6-thioquanine (Porter & DeGregori (2008) Gene Ther. 112: 4466-4474). Also, the drug resistant gene MGMT encoding human alkyl guanine transferase (hAGT) is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze et al., (1999) J. Pharmacol. Exp. Ther. 290: 1467-1474). P140KMGMT-based drug resistant gene therapy has been shown to confer chemoprotection to mouse, canine, rhesus macaques, and human cells, specifically hematopoetic cells (Zielske et al, (2003) J. Clin. Invest. 112: 1561-1570; Pollok et al., (2003) Hum. Gene Ther. 14: 1703-1714; Gerull et al, (2007) Hum. Gene Ther. 18: 451-456; Neff et al., (2005) Blood 105: 997-1002; Larochelle et al., (2009) J. Clin. Invest. 119: 1952-1963; Sawai et al., (2001) Mol. Ther. 3: 78-87).

Glioblastoma multiforme (GBM) is the most common and most aggressive type of primary brain tumor in humans, involving glial cells and accounting for 52% of all parenchymal brain tumor cases and 20% of all intracranial tumors. Despite being the most prevalent form of primary brain tumor, GBMs occur in only 2-3 cases per 100,000 people in Europe and North America. The standard name for this brain tumor is "glioblastoma"; it presents two variants: giant cell glioblastoma and gliosarcoma. Glioblastomas are also an important brain tumor of the canine, and research is ongoing to use this as a model for developing treatments in humans.

Glioblastoma has one of the poorest prognoses among the cancers. Treatment can involve chemotherapy, radiation and surgery, alone or in combination, but the outcome is still typically unfavorable for the patient. For example, the median survival with standard-of-care radiation and chemotherapy with temozolomide is just 15 months. Median survival without treatment is about four and one-half months. There remains, therefore, an urgent need for methods that enhance, replace or supplement current methods of treating such cancers, and in particular those that exhibit transient responses to chemotherapy. Immunotherapy offers such a supplemental procedure if the cytotoxicity of the chemoagent can be circumvented.

SUMMARY

Establishment of immunocompetent cell mediated anti-tumor immunity is often mitigated by the myelosuppressive effects during chemotherapy. The present disclosure provides methods for protecting these immune cells from drug induced toxicities, thereby allowing for the combined administration of immuno- and chemotherapy, an anticancer treatment termed "drug resistant immunotherapy". Using a SIV-based lentiviral system, the drug resistance-conferring genetic element can be delivered into immunocompetent cell lines. Genetically engineered immunocompetent cells developed significant resistance to a specific chemotherapeutic cytotoxic agent compared to non-modified cells, and did not affect their ability to kill target cancer cells in the presence or absence of a chemotherapy agent. Engineering immunocompetent cells to withstand chemotherapy challenges can enhance tumor cell killing when chemotherapy is applied in conjunction with cell-based immunotherapy.

One aspect of the present disclosure, therefore, encompasses methods for reducing a cancer in a patient, comprising the steps of: obtaining a population of isolated cytotoxic immune cells, where the isolated cytotoxic immune cells have been genetically modified to be resistant to a therapeutic agent; administering to a patient in need thereof, an effective amount of the therapeutic agent; and administering to the patient population of isolated genetically modified cytotoxic immune cells, whereupon the cytotoxic immune cells are delivered to the tumor, thereby reducing the cancer in the patient.

In embodiments of this aspect of the disclosure, the isolated cytotoxic immune cells can be γδ T-cells.

In embodiments of this aspect of the disclosure, the step of obtaining a population of isolated cytotoxic immune cells genetically modified to be resistant to a therapeutic agent can comprise: isolating from a subject human or animal a population of cytotoxic immune cells; culturing the isolated population of cytotoxic immune cells, thereby increasing the population of the cells; stably transfecting the population of cytotoxic immune cells with a vector comprising a heterologous nucleic acid sequence operably linked to a promoter, wherein the heterologous nucleic acid sequence encodes a polypeptide conferring to the cell resistance to the therapeutic agent.

Yet another aspect of the present disclosure provides systems for treating a cancer in a patient comprising a cytotoxic therapeutic agent having the characteristics of inhibiting the survival of a cancer cell, and an isolated population of cytotoxic immune cells, where the cytotoxic immune cells genetically modified to be resistant to the therapeutic agent.

Still another aspect of the disclosure provides systems for treating a glioblastoma in a patient comprising a therapeutic agent having the characteristics of inhibiting the survival of a cancer cell and inducing a stress protein in the cancer cell, and an isolated population of cytotoxic immune cells, wherein said cytotoxic immune cells are γδ T-cells, and wherein said γδ T-cells have been genetically modified to be resistant to the therapeutic agent.

In certain embodiments, the invention relates to methods of treating a subject diagnosed with cancer comprising administering a chemotherapy agent to the subject and administering a chemotherapy resistant cell composition to the subject wherein the chemotherapy resistant cell composition comprises cells genetically engineering to express a polypeptide that confers resistance to the chemotherapy agent.

In certain embodiments, the invention relates to isolated compositions comprising natural killer cells wherein greater than about 50%, 60%, 70% 80%, 90%, or 95% of the natural killer cells express a polypeptide that confers resistance to a chemotherapy agent or isolated compositions comprising natural killer cells wherein greater than about 50%, 60%, 70% 80%, 90%, or 95% of the natural killer cells comprise a nucleic acid that encodes a polypeptide that confers resistance to a chemotherapy agent or isolated compositions consisting essentially of natural killer cells comprising a nucleic acid that encodes a polypeptide that confers resistance to a chemotherapy agent. In further embodiments, the polypeptide that confers resistance to a chemotherapy agent is O6 methylguanine DNA methyltransferase (MGMT), a drug resistant variant of dihydrofolate reductase (L22Y-DHFR), thymidylate synthase, and/or multiple drug resistance-1 protein (MDR1).

BRIEF DESCRIPTION OF THE DRAWINGS

Many aspects of the disclosure can be better understood with reference to the following drawings.

FIG. 1 schematically compares a protocol for combining immunotherapy and chemotherapy in the treatment of a cancer, where the immune cells are sensitive (top) and resistant (bottom) to the chemotherapeutic agent. In the non-resistant scheme, an anti-tumor response is provided by cytokines such as IL-2, IL-12, GM-CSF, and the like.

FIGS. 2A and 2B are graphs showing that γδ cells kill glioblastoma cell lines in a dose response fashion (FIG. 2A), and the viability of the glioblastoma cells decrease with increasing amounts of γδ cells (FIG. 2B).

FIG. 2C shows a series of digital images showing the killing of glioblastoma cells.

FIG. 24A illustrates schematics of SIV vector constructs encoding for eGFP (top) and P140KMGMT (bottom).

FIG. 24B is an image of a flow cytometry analysis of NK-92 cells transduced with SIV-eGFP lentivirus.

FIG. 24C is an image of a flow cytometry analysis of TALL-104 cells transduced with SIV-eGFP lentivirus.

FIG. 24D is an image of a flow cytometry analysis of K562 cells transduced with SIV-eGFP lentivirus.

FIG. 28 shows the nucleotide sequences encoding MGMT (SEQ ID NO: 5) and DH1-K (SEQ ID NO: 6) codon optimized for expression in mammalian cells.

SEQUENCE LISTING

Figure 1:
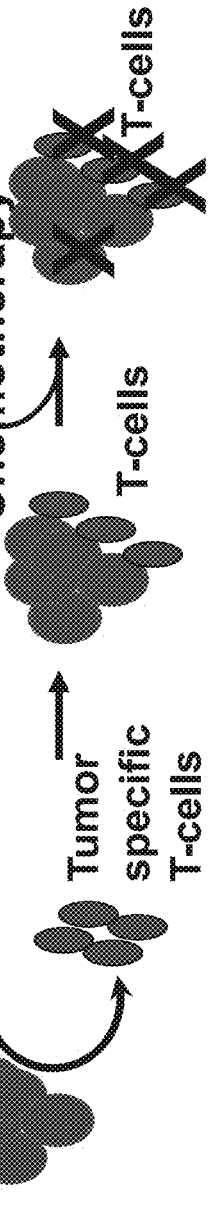
Figure 1:
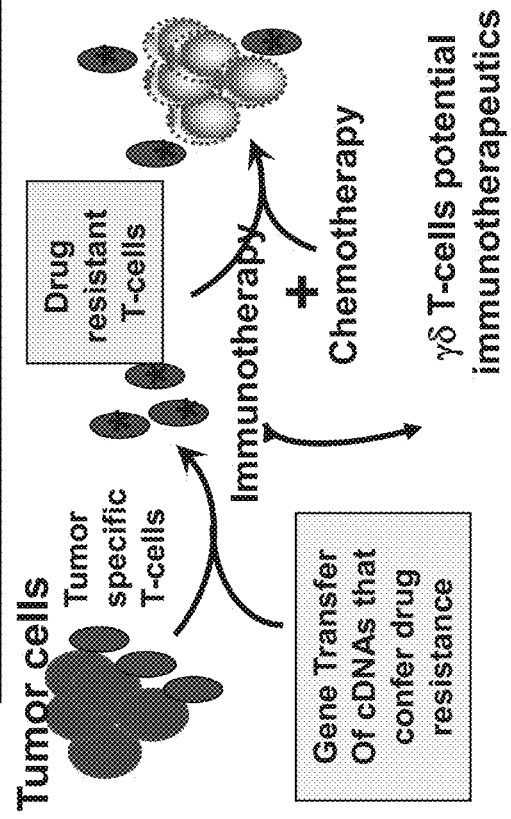

The Sequence Listing is submitted as an ASCII text file [6975-97928-30_Sequence_Listing.txt, Dec. 9, 2019, 2.90 KB], which is incorporated by reference herein.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

By "administration" is meant introducing a compound, biological materials including a cell population, or a combination thereof, of the present disclosure into a human or animal subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used. Direct injection into a target tissue site such as a solid tumor is also contemplated.

The terms "therapeutic agent", "chemotherapeutic agent", or "drug" as used herein refers to a compound or a derivative thereof that can interact with a cancer cell, thereby reducing the proliferative status of the cell and/or killing the cell. Examples of chemotherapeutic agents include, but are not limited to, alkylating agents (e.g., cyclophosphamide, ifosamide), metabolic antagonists (e.g., methotrexate (MTX), 5-fluorouracil or derivatives thereof), antitumor antibiotics (e.g., mitomycin, adriamycin), plant-derived antitumor agents (e.g., vincristine, vindesine, Taxol), cisplatin, carboplatin, etoposide, and the like. Such agents may further include, but are not limited to, the anti-cancer agents trimethotrixate (TMTX), temozolomide, realtritrexed, S-(4-Nitrobenzyl)-6-thioinosine (NBMPR), 6-benzyguanidine (6-BG), bis-chloronitrosourea (BCNU) and camptothecin, or a therapeutic derivative of any thereof.

The term "therapeutically effective amount" as used herein refers to that amount of the compound being administered that will relieve to some extent one or more of the symptoms of a disease, a condition, or a disorder being treated. In reference to cancer or pathologies related to unregulated cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, and/or, (4) relieving to some extent (or, preferably, eliminating) one or more symptoms associated with a pathology related to or caused in part by unregulated or aberrant cellular division, including for example, cancer, or angiogenesis.

The terms "treating" or "treatment" of a disease (or a condition or a disorder) as used herein refer to preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer, these terms also mean that the life expectancy of an individual affected with a cancer may be increased or that one or more of the symptoms of the disease will be reduced.

The terms "subject" and "patient" as used herein include humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. In some embodiments, a system includes a sample and a subject. The term "living host" refers to host or organisms noted above that are alive and are not dead. The term "living host" refers to the entire host or organism and not just a part excised (e.g., a liver or other organ) from the living host.

The term "γδ T-cells (gamma delta T-cells)" as used herein refers to a small subset of T-cells that can specifically bind to a distinct T-cell receptor (TCR) on their surface. A majority of T-cells have a TCR composed of two glycoprotein chains called α- and β-TCR chains. In contrast, in γδ T-cells, the TCR is made up of one γ-chain and one δ-chain. This group of T-cells is usually much less common than αβ T-cells, but are found at their highest abundance in the gut mucosa, within a population of lymphocytes known as intraepithelial lymphocytes (IELs).

The antigenic molecules that activate γδ T-cells are still largely unknown. However, γδ T-cells are peculiar in that they do not seem to require antigen processing and MHC presentation of peptide epitopes although some recognize MHC class IB molecules. Furthermore, γδ T-cells are believed to have a prominent role in recognition of lipid antigens, and to respond to stress-related antigens such as, MIC-A and MIC-B.

The term "cancer", as used herein, shall be given its ordinary meaning, as a general term for diseases in which abnormal cells divide without control. In particular, and in the context of the embodiments of the present disclosure, cancer refers to angiogenesis-related cancer. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult. Benign tumors have less of a tendency to invade and are less likely to metastasize.

Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

The term "reducing a cancer" as used herein refers to a reduction in the size or volume of a tumor mass, a decrease in the number of metastasized tumors in a subject, a decrease in the proliferative status (the degree to which the cancer cells are multiplying) of the cancer cells, and the like.

The terms "isolated" and isolated population of cells" as used herein refers to a cell or a plurality of cells removed from the tissue or state in which they are found in a subject. The terms may further include cells that have been separated according to such parameters as, but not limited to, cell surface markers, a reporter marker such as a dye or label, The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide, or a portion or fragment thereof.

The term "promoter" as used herein refers to the DNA sequence that determines the site of transcription initiation from an RNA polymerase. A "promoter-proximal element" may be a regulatory sequence within about 200 base pairs of the transcription start site.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term "intragenomic" defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The terms "operably" or "operatively linked" as used herein refer to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct tip could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g. the SV40, the Rous sarcoma virus (RSV), and CMV promoters are active in a wide array of cell types, and are termed "constitutive" or "ubiquitous." The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

The termination region which is employed primarily will be one of convenience, since termination regions appear to be relatively interchangeable. The termination region may be native to the intended nucleic acid sequence of interest, or may be derived from another source.

The term "vector" as used herein refers to a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites.

A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

The term "lentiviral-based vector" as used herein refers to a lentiviral vector designed to operably insert an exogenous polynucleotide sequence into a host genome in a site-specific manner Lentiviral-based targeting vectors may be based on, but is not limited to, for example, HIV-1, HIV-2, simian immunodeficiency virus (SIV), or feline immunodeficiency virus (FIV). In a preferred embodiment, the lentiviral-based targeting vector is an HIV-based targeting vector. This vector may comprise all or a portion of the polynucleotide sequence of HIV.

The terms "transformation", "transduction" and "transduction" all denote the introduction of a polynucleotide into a recipient cell or cells.

DISCUSSION

Figure 3:
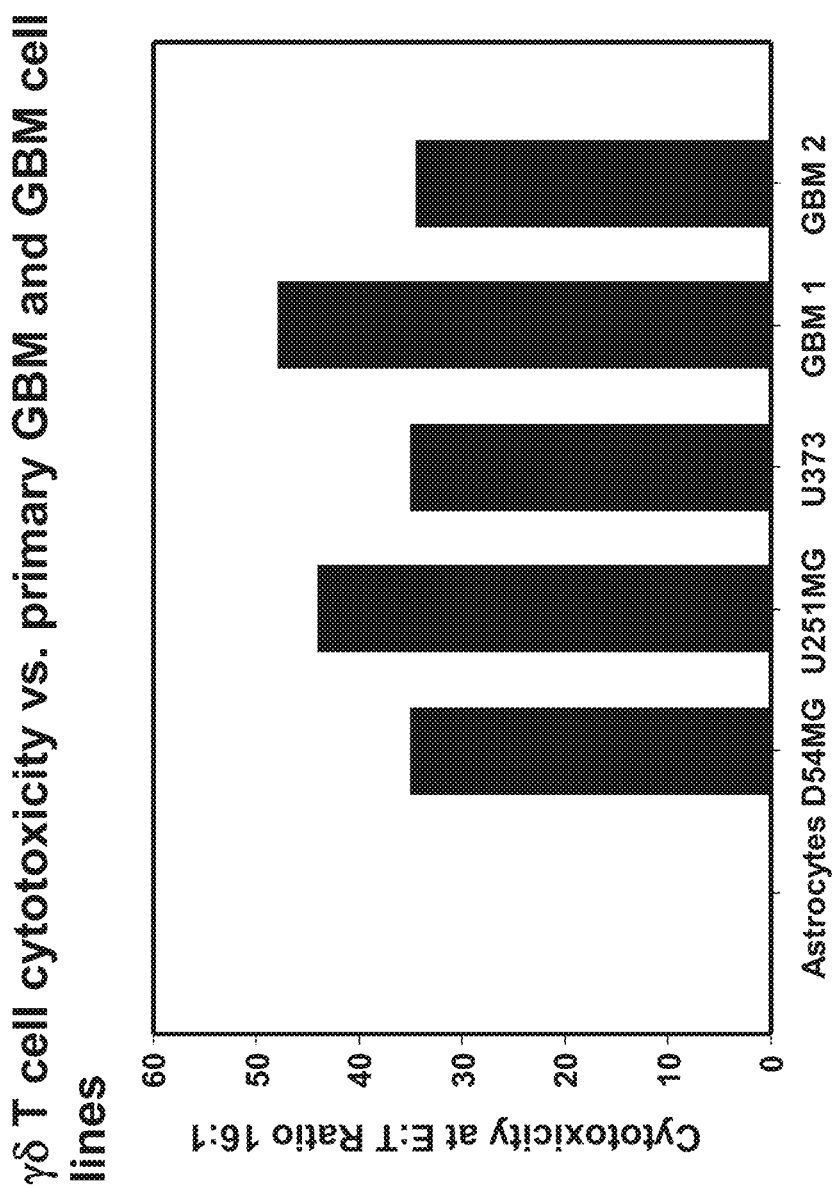
FIG. 3 shows a bar graph illustrating the cytotoxicity of isolated γδT-cells against several cultured glioblastoma cell isolates, including: cultured primary (GBM 1 and GBM 2) glioblastomal cells and cultured cell lines D54MG, U251MG, and U373.
Figure 4:
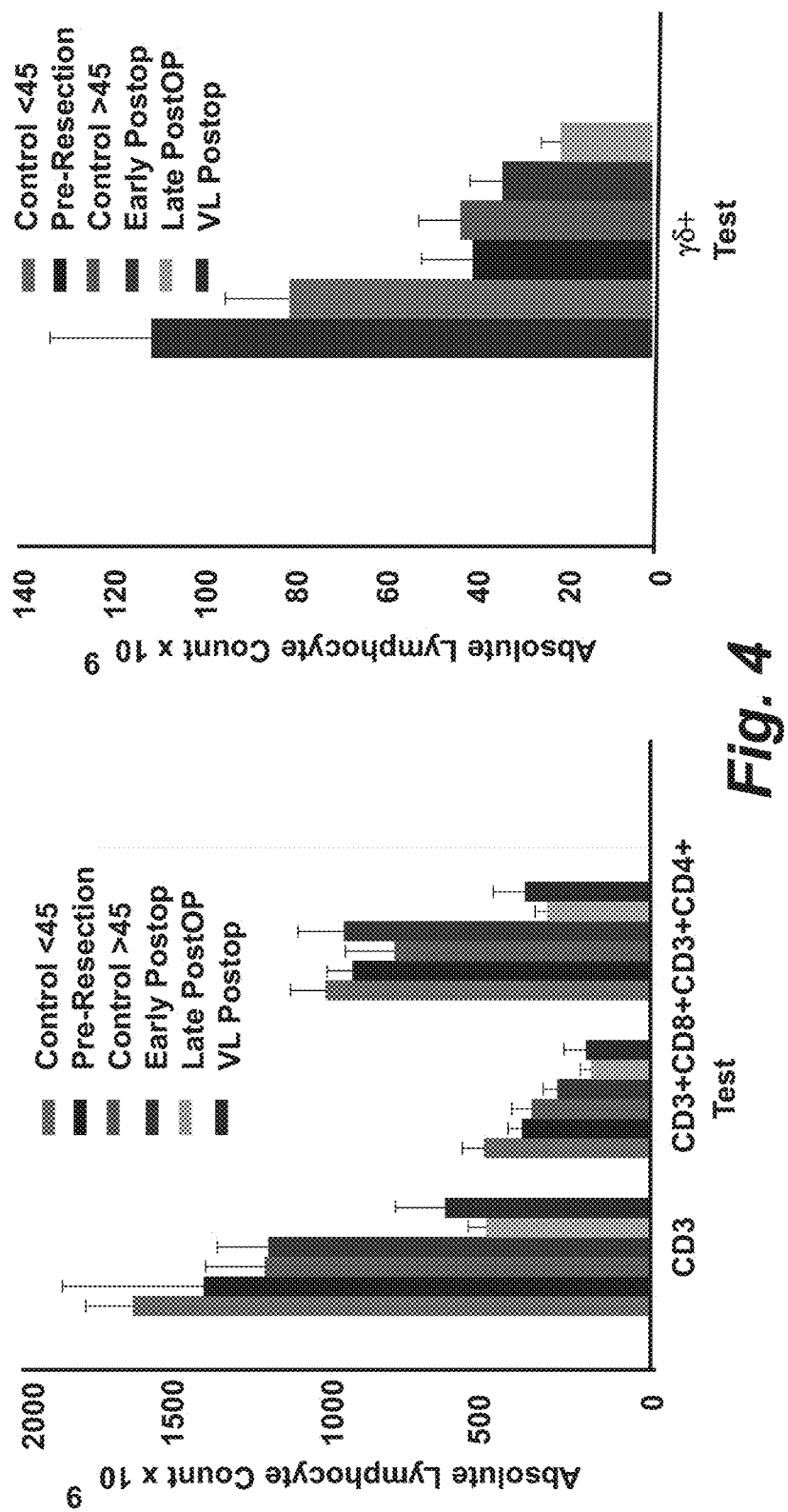
FIG. 4 shows a pair of bar graphs illustrating that cells involved in the adaptive immune response are sensitive to current glioblastoma treatment regimens (left). γδ cells are similarly sensitive (right).
Figure 5:
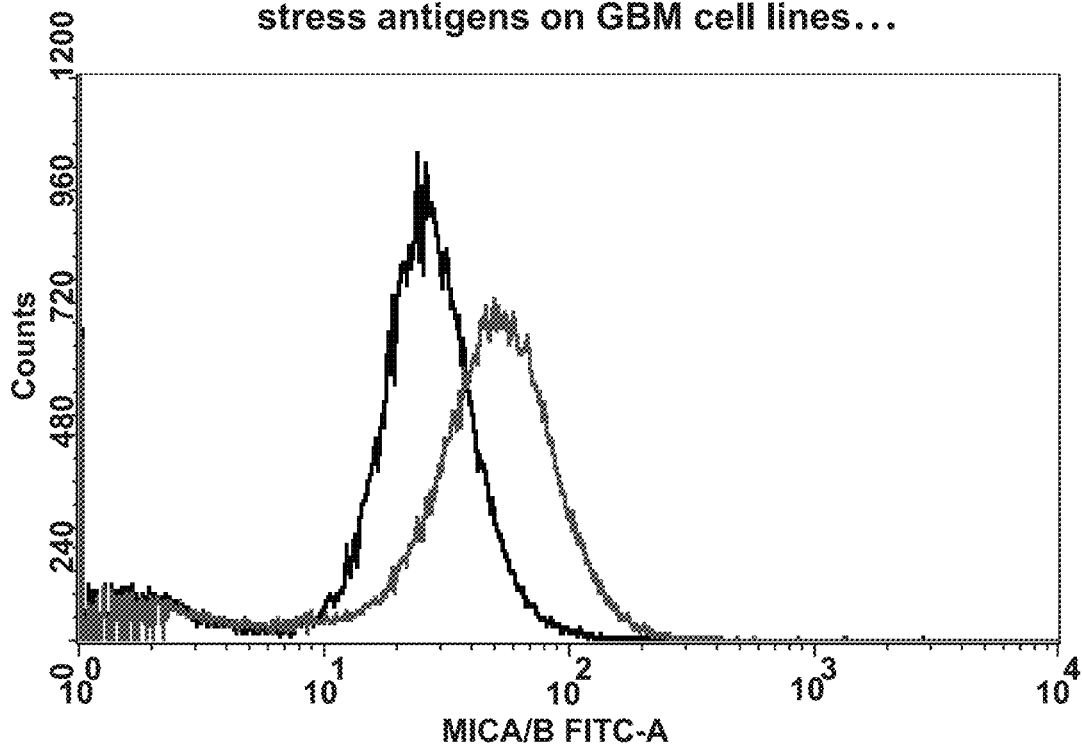
FIG. 5 is a graph showing the expression of cell surface stress antigens MICA/B induced by the chemotherapeutic agent Temozolamide (TMZ).
Figure 6:
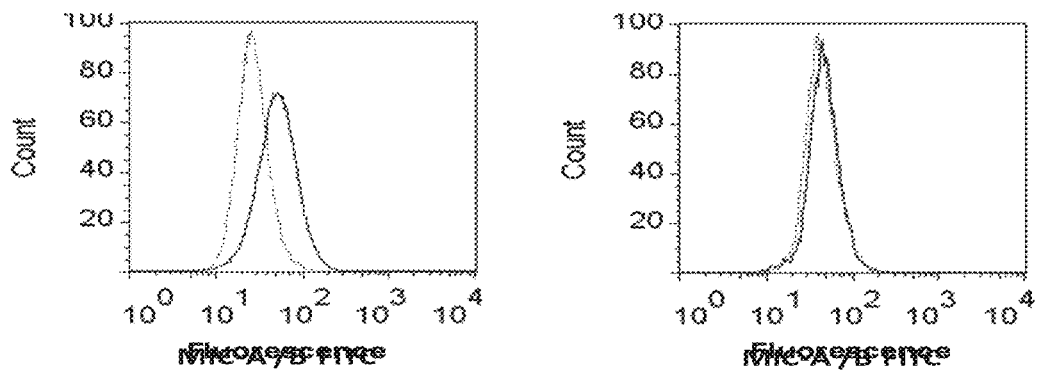
FIG. 6 is a graph showing that the expression of cell surface stress antigens MICA/B induced by the chemotherapeutic agent Temozolamide (TMZ) is transient.

A major limitation to chemotherapy treatments for cancer is drug induced immune toxicity. This results, upon administration of the therapeutic agent, in the killing of immunocompetent cells and loss of an effective immune system that would otherwise ward off undesirable infections or provide a defense against cancer cells. One strategy to combat the severe toxic effects of chemotherapy is to genetically engineer blood or marrow cells by the introduction of retroviral vectors designed to express cDNA sequences that confer drug resistance. The introduction of drug resistant genes into hematopoietic stem cells (HSCs) results in transgene expression throughout the entire host hematopoietic system, including immunocompetent cells such as T cells and natural killer cells, after transplantation of gene-modified cells back into a recipient patient, as described by McMillin et al., (2006) Human Gene Therapy 17:798-806. The patient can then develop an active immune system while at the same time undergoing chemotherapy. However, in the case of HSC transgene expression, over time not all of the T cells and natural killer cells in the subject express the drug resistant gene. For example, McMillin et al. (2005) discloses that less than 50% of NK-cells contained an expressing marker 8 week post-transplant. See FIG. 3 of McMillin et al.

An alternative strategy would be to selectively genetically modify cytotoxic immunocompetent cells that can actively target those cancer cells able to resist the simultaneous administration of a chemotherapeutic agent, thereby effectively eliminating most if not all cancer cells from the patient.

In certain embodiments, the invention relates to isolated compositions comprising natural killer cells wherein greater than about 50% of the natural killer cells express a polypeptide that confers resistance to a chemotherapy agent. In other embodiments, the invention relates to isolated compositions comprising natural killer T-cells wherein greater than about 50% of the natural killer T-cells comprise a nucleic acid that encodes a polypeptide that confers resistance to a chemotherapy agent. In other embodiment the invention relates to isolated compositions consisting essentially of natural killer T-cells comprising a nucleic acid that encodes a polypeptide that confers resistance to a chemotherapy agent. In certain embodiments the polypeptide that confers resistance to a chemotherapy agent is $O^6$ methylguanine DNA methyltransferase (MGMT), a drug resistant variant of dihydrofolate reductase (L22Y-DHFR), thymidylate synthase, multiple drug resistance-1 protein (MDR1).

In certain embodiments, the invention relates to methods of treating a subject diagnosed with cancer comprising: administering a chemotherapy agent to the subject and administering a chemotherapy resistant natural killer cell composition to the subject wherein the chemotherapy resistant natural killer cell composition comprises natural killer cells genetically engineering to express a polypeptide that confers resistance to the chemotherapy agent.

The present disclosure encompasses methods whereby immunocompetent cells are selectively protected from the toxic effects of chemotherapy, thereby allowing co-administration of chemotherapy and cell-based immunotherapy, and hence termed drug resistant immunotherapy. The feasibility of using drug resistant immunotherapy in the context of drug-resistant hematopoietic cells has been shown (Cesano et al., (1998) Anticancer Res. 18: 2289-2295). Mouse bone marrow cells were genetically engineered by retroviral-mediated introduction of a cDNA encoding for a mutant form of DHFR, i.e. L22Y-DHFR that confers resistance to trimetrexate (TMTX). Mice were transplanted with gene-modified bone marrow cells that resulted in transgene expression in all hematopoietic lineages. The mice were then treated with the immunotherapeutic agent anti-CD137, TMTX alone, or a combination of anti-CD137 and TMTX.

In mice inoculated with AG104 sarcoma cells, TMTX chemotherapy reduced the efficacy of an anti-CD137 antibody in mice transplanted with non-modified cells that were sensitive to the TMTX. However, when mice were protected against chemotherapy-induced toxicity through transplantation of L22Y-DHFR-expressing bone marrow, the combined treatment of TMTX and anti-CD137 resulted in complete eradication of tumors in 100% of animals. The present disclosure provides evidence that genetically engineered human immunocompetent cells can be used in the context of drug resistance immunotherapy, rather than genetically modifying the entire hematopoietic system. The ability to provide to a patient a genetically-modified population of cytotoxic immunocompetent cells, and particular if delivered locally to the site of a tumor, would allow for immunotherapy in conjunction with chemotherapy without necessarily undergoing bone marrow transplantation.

NK-92 and TALL-104 cells are representative immune-effector cell lines since both of these cell types recognize and kill a wide range of malignant cells, including K562 cells (Sawai et al., (2001) Mol. Ther. 3: 78-87; Tam et al., (1999) J. Hematother. 8: 281-290). The highly potent cytotoxic human NK cell line NK-92 is an interleukin-2 (IL-2)-dependent human natural killer cell line with functional and phenotypic characteristics of activated NK cells (Gong et al., (1994) Leukemia 8: 652-658). NK-92 cells are effectors of the innate immune system, which play an important role in host responses against viruses and tumor cells Due to the high cytotoxicity against a broad spectrum of primary and established tumor cells at low effector:target ratios and against primary leukemia in SCID mice (Gong et al., (1994) Leukemia 8: 652-658; Yan et al., (1998) Clin. Cancer Res. 4: 2859-2868; Tam et al., (1999) J. Hematother. 8: 281-290) makes them a reasonable candidate as a drug resistant immune effector cell (Yan et al., (1998) Clin. Cancer Res. 4: 2859-2868; Tam et al., (1999) J. Hematother. 8: 281-290). TALL-104 cells are an interleukin 2-dependent leukemic T cell line that has surface markers typical of those found on both cytotoxic T lymphocytes and natural killer cells. TALL-104 cells lyze tumor cells in a non-HLA-restricted fashion (Tam et al., (1999) J. Hematother. 8: 281-290). Adoptive immunotherapy with TALL-104 has induced long-term complete or partial remissions in tumor bearing animals (Tam et al., (1999) J. Hematother. 8: 281-290; Geoerger et al., (2000) Neuro Oncol. 2: 103-113). Similar to NK-92 cells, we used TALL-104 cells as immunocompetent cells for our proof-of-concept studies since these cells can be expanded in culture indefinitely to provide an unlimited source of effector cells with stable tumoricidal activity.

P140K-MGMT-genetically engineered NK-92 and TALL-104 cells were resistant to TMZ and had cytotoxic activities similar to the non-modified cells. Additionally, the gene-modified cells showed cytolytic activities similar to non-transduced cells after drug selection. Therefore, genetic modification of these cells does not affect their cytotoxic activity.

Drug resistant immunotherapy was evaluated in a series of cytotoxic assays, in the presence and absence of a cytotoxic drug. Dasqupta et al., (2010) Biochem. Biophys. Res. Comm 391:170-175. Importantly, gene-modified immunocompetent cells displayed significant cytolytic activities toward drug resistant tumor cells in the presence of drug. In contrast, non-modified immunocompetent cells were ineffective at tumor killing when drug was administered. Combined, these results demonstrate that in the presence of a cytotoxic chemotherapeutic drug, gene-modified effector cells remain active, and a greater level of target cancer cell killing was observed after treating gene-modified effector cells and non-modified target cells compared to non-modified effector cells and drug resistant target cells. Accordingly, genetically-modified drug resistant immunocompetent cells could be engineered to survive the cytotoxic effects of chemotherapeutic agents and the effectiveness of tumor killing significantly increases during a chemotherapy challenge.

The present disclosure provides data that drug-resistant immunocompetent effector cells are superior cytotoxic effectors during a chemotherapy challenge. This is a significant finding which can be combined with current cell-based and adoptive immunotherapies. It has been shown that regression of large, vascularized tumors occurs in patients with refractory metastatic melanoma. However, for maximum effectiveness, a lympho-depleting regimen is typically necessary prior to autologous lymphocyte cell transfer (Chinnasamy et al., (2004) Hum. Gene Ther. 8: 758-769).

The generation and expansion of drug-resistant lymphocytes (as opposed to the entire hematopoietic system) ex vivo can allow, in this setting, for administration of immunocompetent cell-based therapy concurrently with chemotherapy, potentially improving tumor clearance while anti-tumor immunity is established and maintained. In this scenario, non-transduced lymphocytes can be depleted using a selective chemotherapy treatment, which could be continually applied during the administration of adoptive immunotherapy. The co-administration of chemo- and immuno-therapies would then lead to long-term tumor clearance.

It was shown, however, that the growth of CML cells in mice transplanted with bone marrow engineered to confer resistance to MTX can be exacerbated by the administration of chemotherapy (Rosenberg & Dudley (2004) Proc. Natl. Acad. Sci. USA. 101: 14639-14645). Thus chemotherapy treatment in the context of gene-modified whole bone marrow protection may induce secondary effects such as immune suppression that allow some cancers to survive a drug challenge. Base on the results of the present disclosure, however, instead of transplanting drug resistant hematopoietic stem cells, a more effective strategy involves transplantation of drug resistant immunocompetent lymphocytes.

Additionally, it was recently shown that melanoma and glioma cell lines are sensitive to the combination of TMZ and antifolates (Sweeney et al., (2002) J. Pharmacol. Exp. Ther. 300: 1075-1084). In one embodiment of the methods of the disclosure, therefore, retroviral transfer of dual vectors that co-express drug resistant variants of DHFR, such as, L22Y-DHFR, together with P140K-MGMT would increase tumor cell killing by allowing effective cytotoxic immunotherapy while administering a combination of chemotherapeutic agents. Expression of DHFR mutants, for example, can provide resistance to antifolates such as methotrexate and trimetrexate, while MGMT expression can provide resistance to monofunctional methylating agents such as dacarbazine and procarbazine as well as bifunctional chloroethylating agents such as BCNU, ACNU or TMZ.

Accordingly, a series of combinatorial cytotoxicity assays was performed with non-modified and gene-modified effector and target cells. To determine the effects of TMZ on non-modified cells, cytotoxicity assays were performed whereby non-modified effector cells were mixed with gene-modified target cells in either the absence or presence of 200 µM 6-BG/TMZ.

Gene-modified target cells were used to eliminate the effects of chemotherapy on the target cells (gene-modified target cells were resistant to TMZ at this drug concentration). Before these studies were initiated, the sensitivity of gene-modified K562 cells to NK92 and Tall-104 cells was determined. A 4 hr cytotoxicity assay was conducted where non-modified effector cells (E) were incubated with either non-modified target (T) or gene-modified target (Tm) cells at an effector to target ratio of 10:1, as shown in FIG. 27, in the absence of drug. The cytotoxicities of both the non-modified effector cell lines (NK92 and TALL-104) toward either non-modified or gene-modified target cells were comparable ($P_{NK-2}$=0.8441, $P_{TALL-014}$=0.6349). Thus genetic modification of the target cells did not affected their lyses by the immunocompetent cells.

Cytotoxic assays were then conducted using non-modified effector cells and gene-modified target cells in the presence of TMZ. A significant decrease in both NK-92 and TALL-104 cell mediated lysis was observed when compared to gene-modified target cells in the absence of drug treatment (see FIG. 27; $P_{NK-92}$=0.0003, $P_{TALL-014}$=0.0008). Thus, the clearance of drug resistant tumor cells by non-modified immunocompetent cells is severely limited after a chemotherapy challenge.

To compare the killing effectiveness of non-modified and gene-modified immune effector cells during drug treatments, cytotoxicity assays were conducted whereby non-modified or P140KMGMT-modified effector cells (Em) were incubated with gene-modified target cells (Tm) and 200 µM 6-BG/TMZ.

When compared to non-modified effector cells, genetically-modified NK-92 cells lyzed target cells significantly better after being treated with 6-BG/TMZ, as shown in FIG. 27 Panel A ($P_{NK-92}$=0.0001). Thus, in the presence of drug, P140KMGMT-modified immunocompetent cells were active in killing tumor cells. Under identical conditions, however, genetically engineered TALL-104 cells had only a modest increase in cytotoxic activity (FIG. 27B).

To determine the effectiveness of drug resistant tumor cells during a chemotherapy challenge when the target cells are sensitive to the drug treatment, gene-modified effectors, i.e. P140KMGMT-NK-92 and P140KMGMT-TALL-104 cells, were incubated with non-modified, drug-sensitive target cells and 200 µM 6-BG/TMZ. The cytotoxicities of these drug resistant immunocompetent cells were then compared with the cytotoxicities achieved using drug-sensitive immunocompetent cells, as shown in FIGS. 27 C and 27D.

Compared to the killing of gene-modified target cells by non-modified effector cells, there was a significant increase of about 4.5-fold and 2.5-fold killing of non-modified target cells by the genetically modified NK-92 and TALL-104 cells, respectively ($P_{NK-92}$=0.0012, $P_{TALL-014}$=0.0011). These data demonstrate that P140KMGMT-modified NK-92 and TALL-104 cells function as potent effectors in the presence 6-BG/TMZ, and that the drug resistant immunocompetent cells, when used concurrently with chemotherapy, can significantly enhance the killing of target cells.

Embodiments of the present disclosure encompass methods of treating cancers, and in particular cancerous tumors. The methods of the disclosure combine the use of chemotherapeutic agents that can kill or reduce the proliferation of cancerous cells, with immunotherapy to effectively eliminate those cancerous cells that develop drug resistance or otherwise escape the chemotherapeutic agent. The methods of the present disclosure provide for isolating cytotoxic immune cells, including, but not limited to, γδ T-cells either from a patient to be treated or from another source, as described, for example, by Lamb L. S. in U.S. Pat. No. 7,078,034, incorporated herein by reference in its entirety. The isolated cells may then be transfected with a nucleic acid vector comprising a heterologous nucleotide sequence encoding a polypeptide that confers resistance to a selected chemotherapeutic agent to the cell. The patient in need of treatment for a cancer, and in particular a tumor, may then receive a dose, or doses, of the transfected T-cells before, after or with the chemotherapeutic agent. The agent itself, while intended to be toxic to the targeted cancer cells, and will reduce the proliferation and viability of the cells, may also induce the formation on the cell surface of the cancer cells of stress-related proteins. Transfected γδ T-cells, for example, have the characteristic of being able to recognize and therefore target such stress-related ligands, thereby specifically or preferentially targeting the cancer cells.

The transduction of a population of cytotoxic immune cells, such as γδ T-cells with a heterologous nucleic acid encoding an exogenous polypeptide conferring resistance to the chemotherapeutic agent can ensure that the immunotherapeutic cells are not adversely affected by the agent (drug). The result is that the chemotherapy and the immunotherapy cooperate to efficiently reduce the tumor mass or eliminate the cancerous cells. The data provided herein indicate that an increase in the survival outcome of a treated animal can be achieved.

It is contemplated that the genetically modified cytotoxic immune cells such as γδ T-cells may be delivered to the targeted tumor directly by such as, but not limited to, direct injection into the tumor mass, delivery to a blood vessel entering the tumor mass, or a combination of both. For example, it is contemplated that the cells may be delivered to a glioblastomal mass in the brain of a patient by direct implantation through a cannulated needle inserted into the tumor mass.

The methods of the disclosure compare with other methods that combine chemotherapeutic and immunologic approaches to treating cancers. For example, as shown in FIG. 1, cytokines and other factors that can stimulate the immune system, including the innate system, may be administered to a patient systemically, resulting in expansion of many classes of cells of the patients entire immune system. However, when the chemotherapeutic agent is then administered, the toxicity of the agent can effectively reduce or destroy the immune system cells themselves, thereby eliminating the potential benefits of an expanded immune system.

Figure 13:
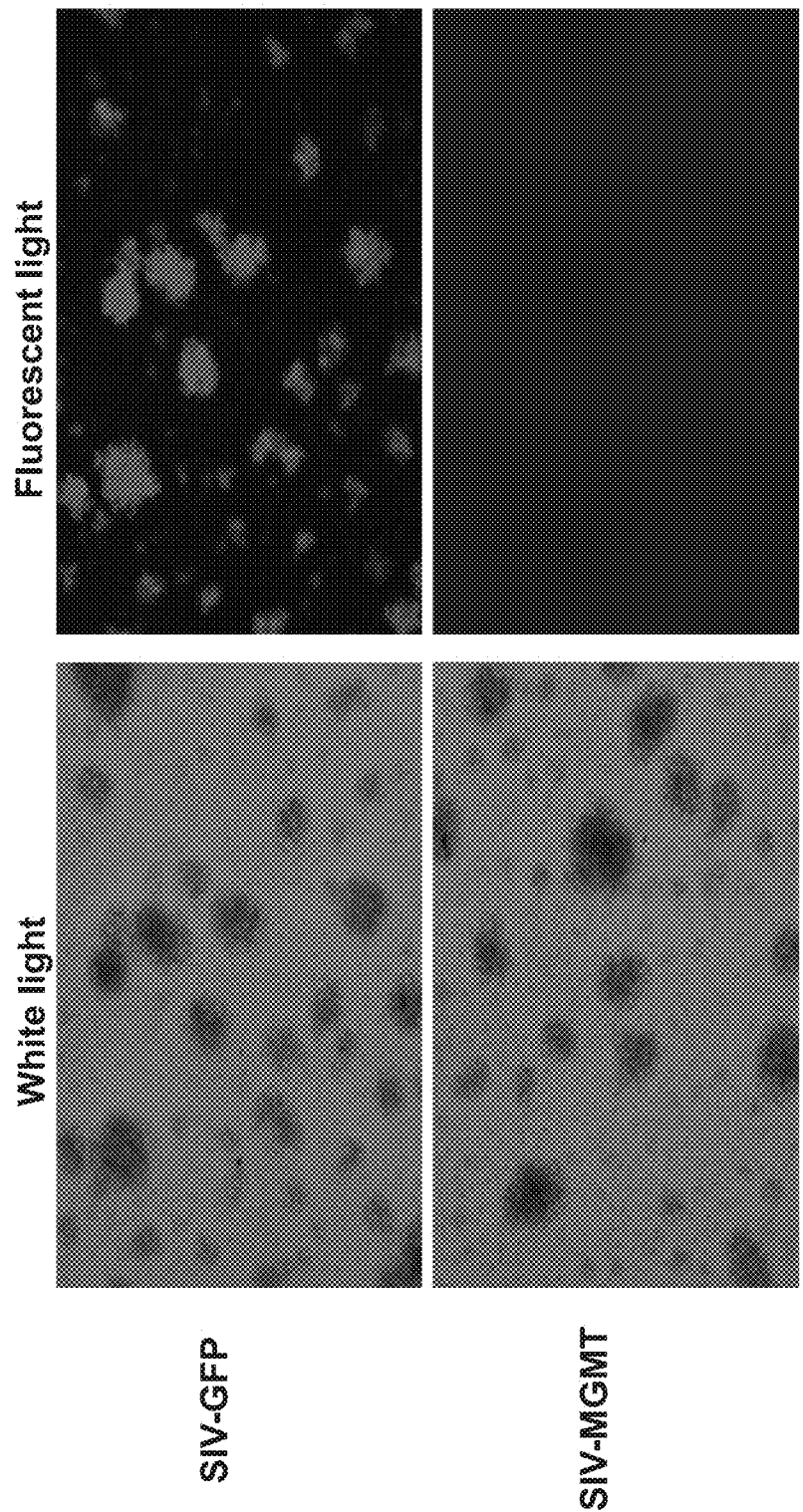
FIG. 13 is a series of digital photographs illustrating transduction of γδT-cells with SIV-GFP or SIV-MGMT constructs. The top panels show high transduction efficiency using a GFP-encoding construct. As expected, no fluorescence is observed with MGMT (bottom panel).
Figure 14:
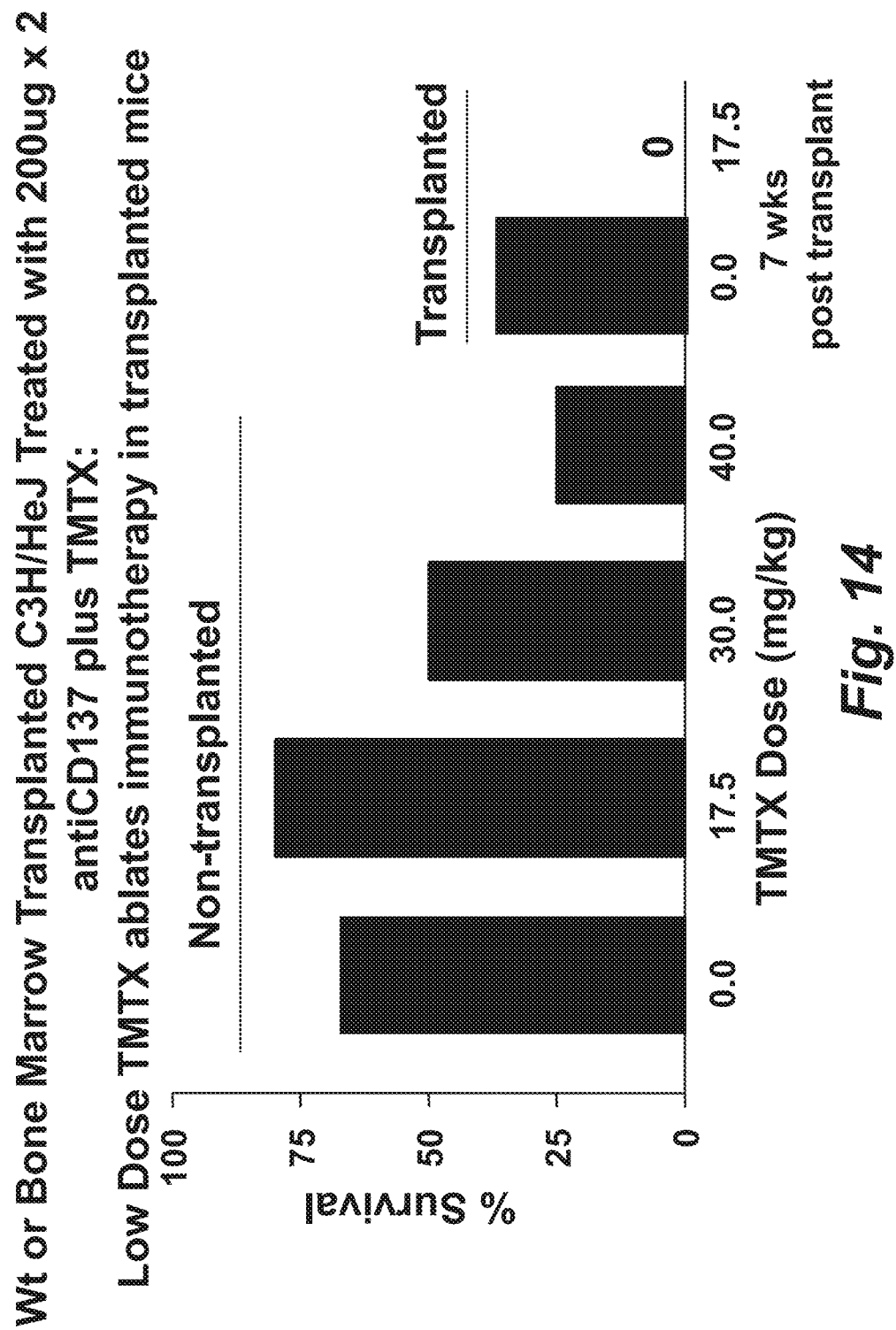
FIG. 14 is a graph showing that the administration of a chemotherapeutic agent to an anti-cancer regimen, which also requires T-cell expansion, decreases the effectiveness of the cell-based treatment. This decrease is very pronounced when the mice have undergone a bone marrow transplant procedure, which is a common procedure for patients undergoing treatment for several types of cancer.
Figure 15:
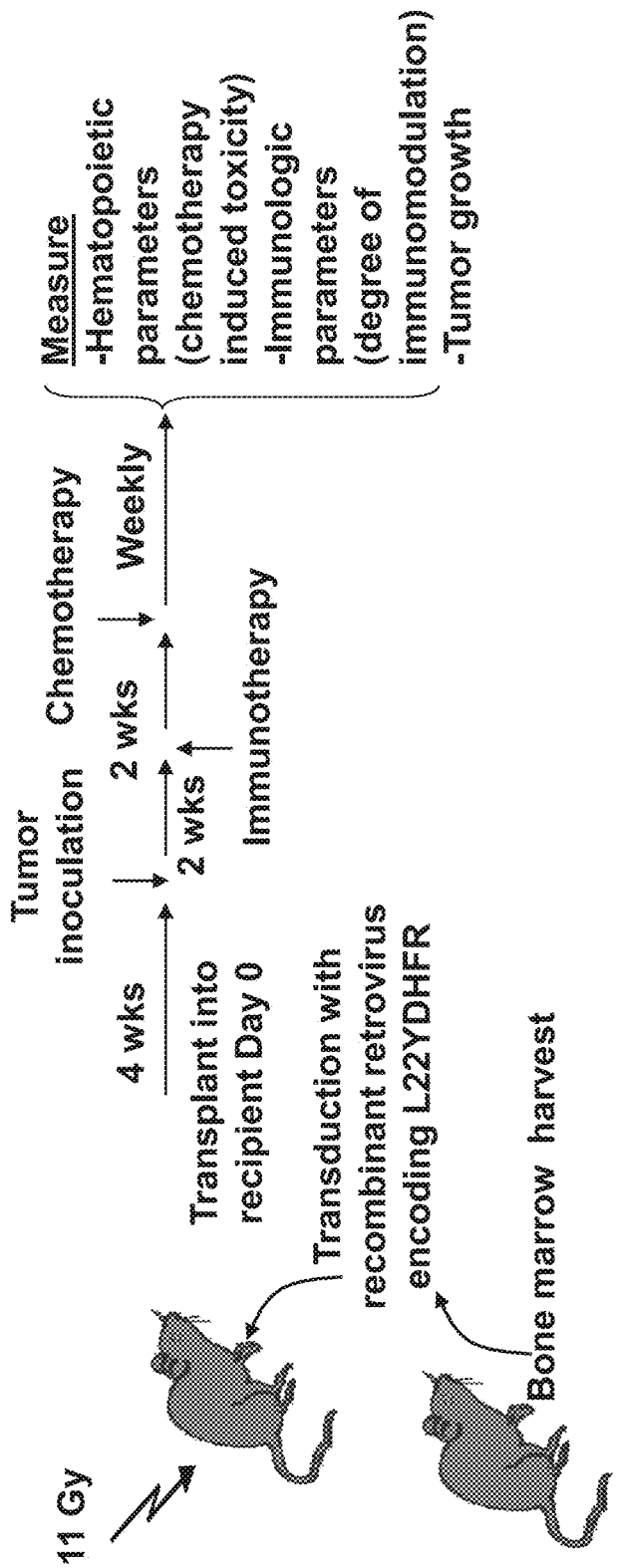
FIG. 15 schematically shows an experimental protocol for treating a cancer with drug resistant immune cells. In this protocol, bone marrow was harvested from mice and transduced with a recombinant lentivirus vector comprising the heterologous nucleic acid sequence encoding the L22YDHFR variant. The transduced cells were transplanted into irradiated recipient mice. After 4 weeks AG104 sarcoma cells were transplanted. Two weeks later the mice would receive immunotherapy comprising anti-CD137 antibodies followed by chemotherapy (TMTX).
Figure 16:
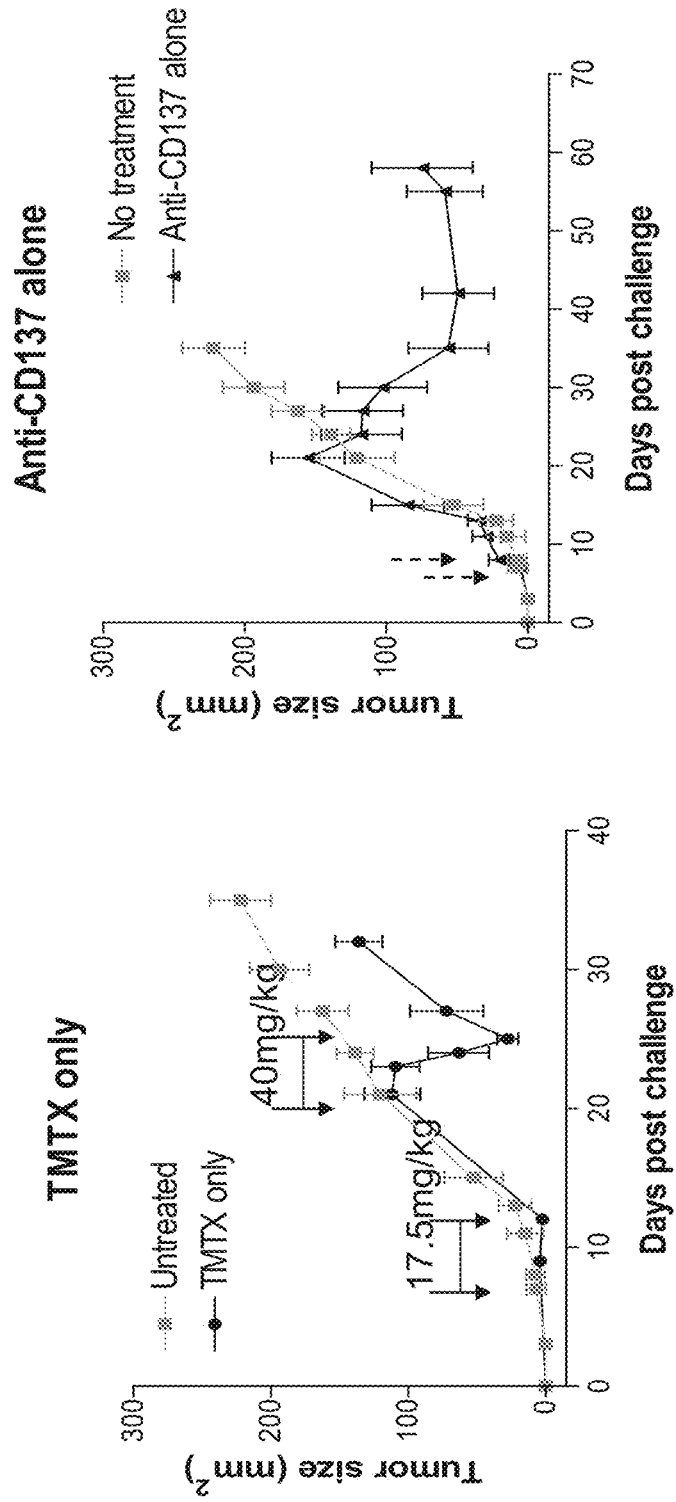
FIG. 16 shows a pair of graphs illustrating the effect of chemotherapy (TMTX) treatment alone or immunotherapy alone (anti-CD137 antibody stimulation of cytotoxic lymphocytes). In each case the protocol scheme shown in FIG. 15 was followed.
Figure 17:
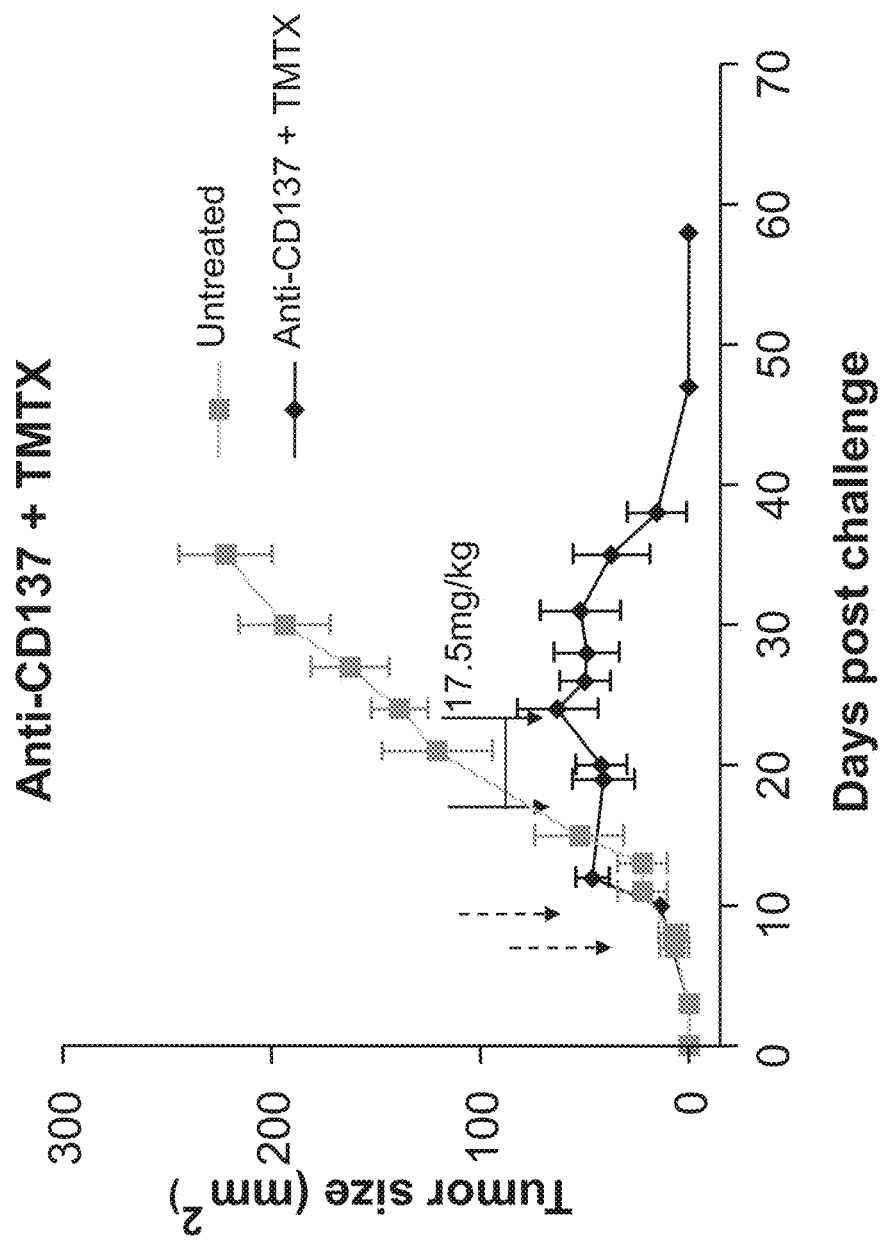
FIG. 17 shows a graph illustrating the rapid and prolonged reduction in AG104 tumor size with the immunotherapy-chemotherapy combination where the immune system of the tumor-bearing mice was rendered TMTX-resistant by transduction with L22YDHFR.
Figure 18:
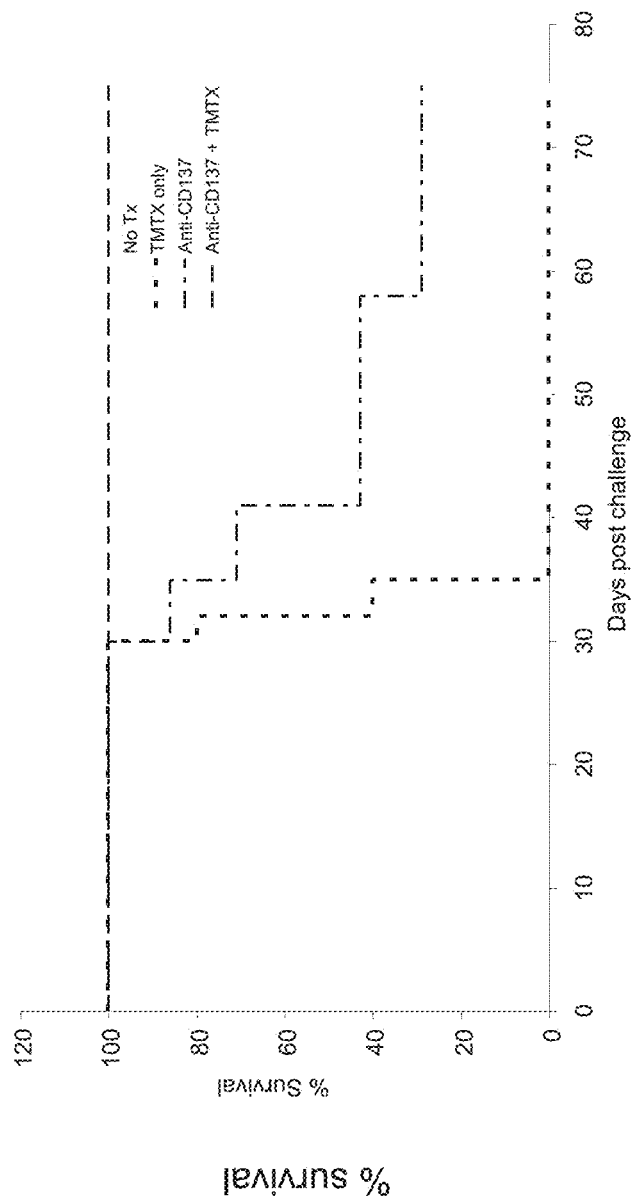
FIG. 18 shows a survival chart for DHFR-bearing mice transplanted with AG104 sarcoma cells and treated with TMTX and/or anti-CD137 immunotherapy.
Figure 19:
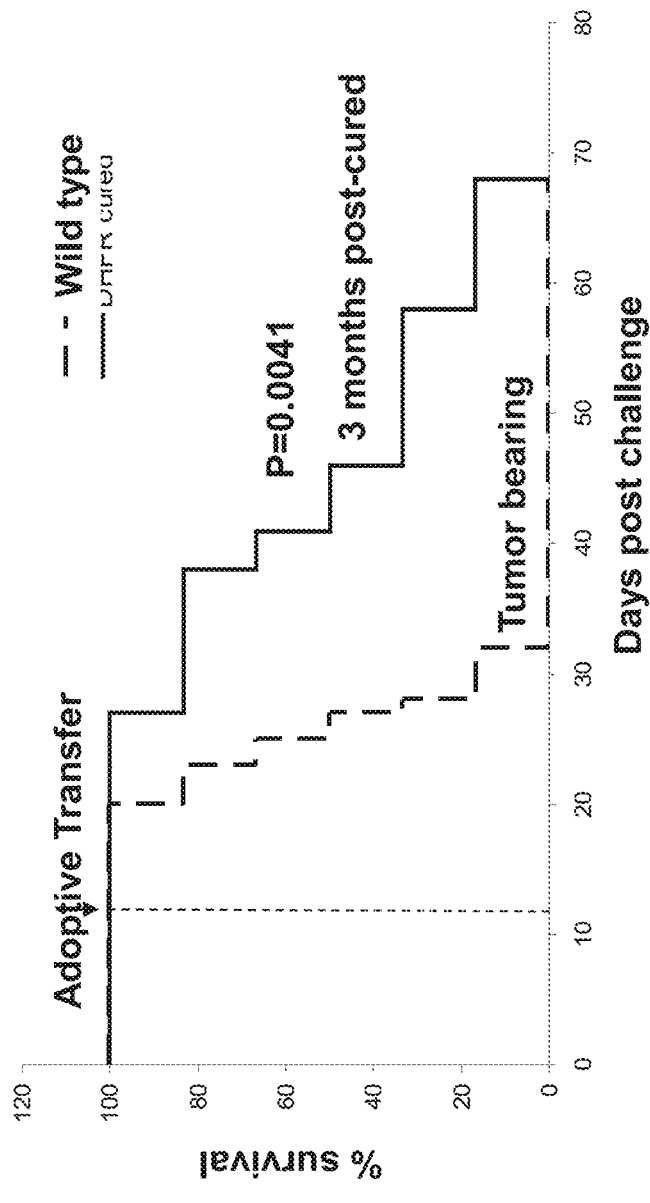
FIG. 19 shows a survival chart for mice receiving splenocytes isolated from tumor-bearing and DHFR-cured mice and then challenged with AG104 sarcoma cells.

An alternative protocol, as shown in FIG. 17, comprises isolating bone marrow cells from a subject and transducing the cells with a nucleic acid vector, such as, but not limited to, a lentiviral vector, where the vector comprises a heterologous nucleic acid sequence encoding a polypeptide that can confer resistance to the chemotherapeutic agent selected for use in treating a cancer, as shown in FIG. 13, for example. In an experimental system, as shown in FIG. 17, the transduced marrow cells may be transplanted into a recipient subject that has had the immune system destroyed by high-level radiation. If these subjects then receive a tumor cell inoculation they will develop a tumor(s), as shown in FIGS. 18 and 19, and discussed in McMillin et al., (2006) Hum. Gene Therapy 17: 798-806, incorporated herein by reference in its entirety. If the subject then receives either the selected chemotherapeutic agent or an inducer of cancer-targeting immune cells (in this case by administering anti-CD137 antibodies), then reductions in the sizes of tumors (in FIGS. 18 and 19, AG104 sarcoma tumors) are observed.

In some protocols that combine immunotherapy and chemotherapy to treat cancers in a subject human or animal patient, cytokines (IL-2, IL-12, GM-CSF, and the like) may be delivered to a patient to boost the formation of cytotoxic lymphocytes. In other methods, an anti-CD137 specific antibody may be employed. CD137 is a member of the tumor necrosis factor (TNF)/nerve growth factor (NGF) family of receptors and is expressed by activated T- and B-lymphocytes and monocytes; its ligand has been found to play an important role in the regulation of immune responses. An anti-CD137 monoclonal antibody can specifically bind to CD137-expressing immune cells such as activated T-cells and freshly isolated mouse dendritic cells (DCs), thereby stimulating an immune response, in particular of a cytotoxic T cell response, against tumor cells.

Figure 20B:
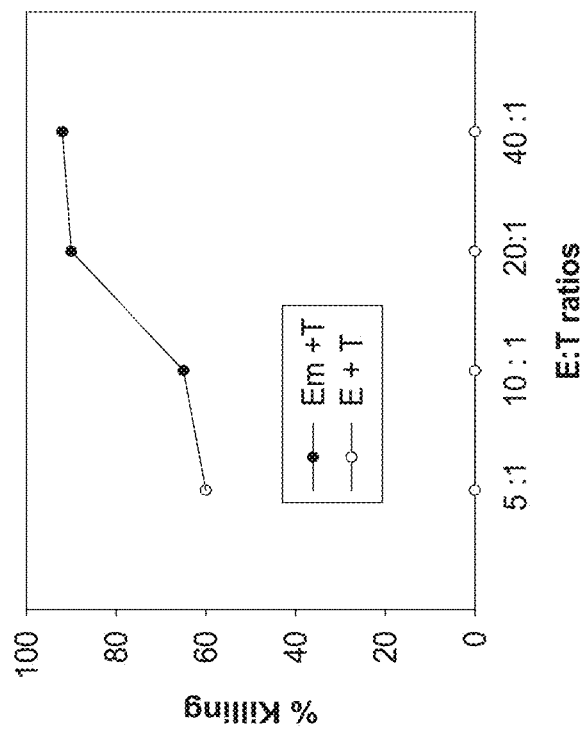
FIG. 20A and FIG. 20B show data suggesting genetically engineered γδ T cells killed both wt and TMZ resistant GBM cells in the presence of agent. Non-modified γδ T cells are not active in the presence of TMZ. Em is gene-modified γδ T cells. E is non-modified γδ T cells. T is SB19 TMZ resistant.
Figure 20A:
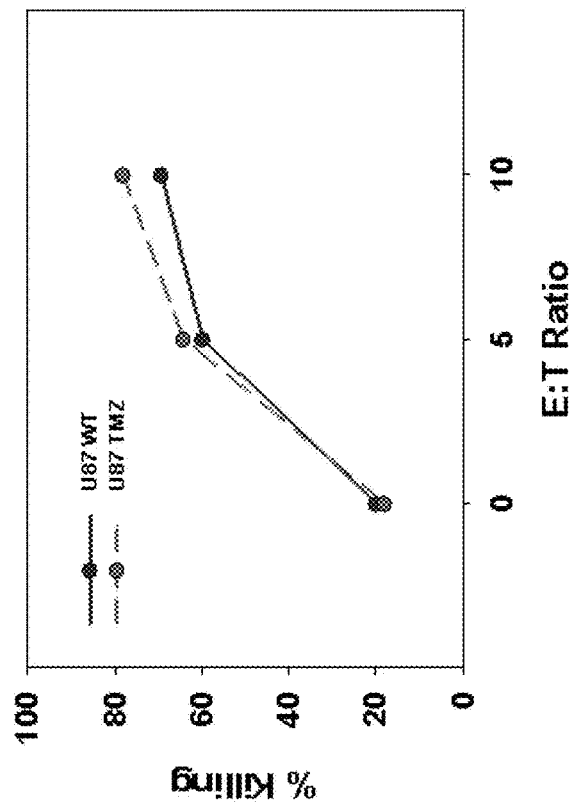
Figure 21:
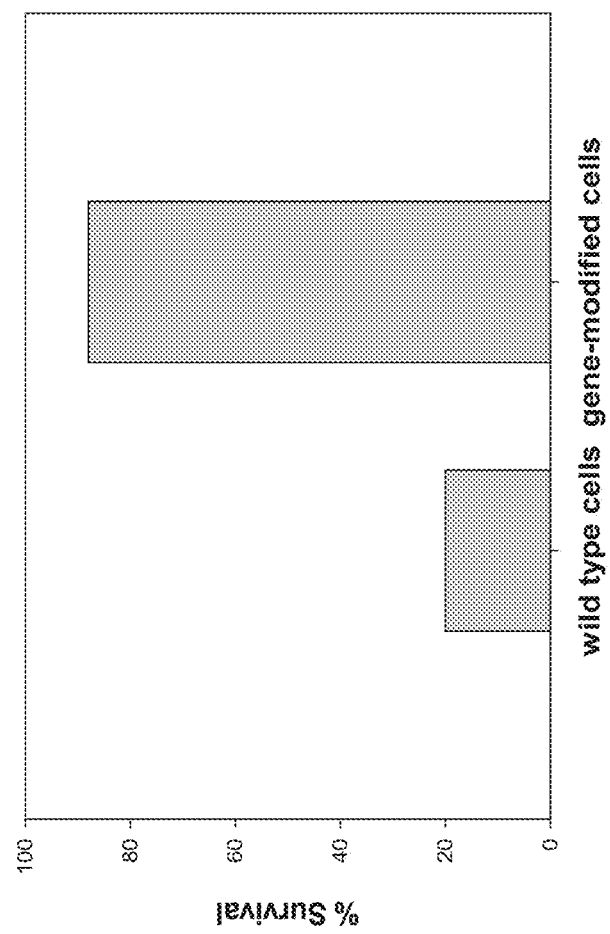
FIG. 21 shows data suggesting genetic modification of γδ T cells confers resistance to TMZ. γδ T cells were transduced (MOI=20) with SIV-MGMT-DHFR at day 8 of expansion and cell viability was measured at day 14. Viability was assessed by uptake of ToPro Iodide.
Figure 22:
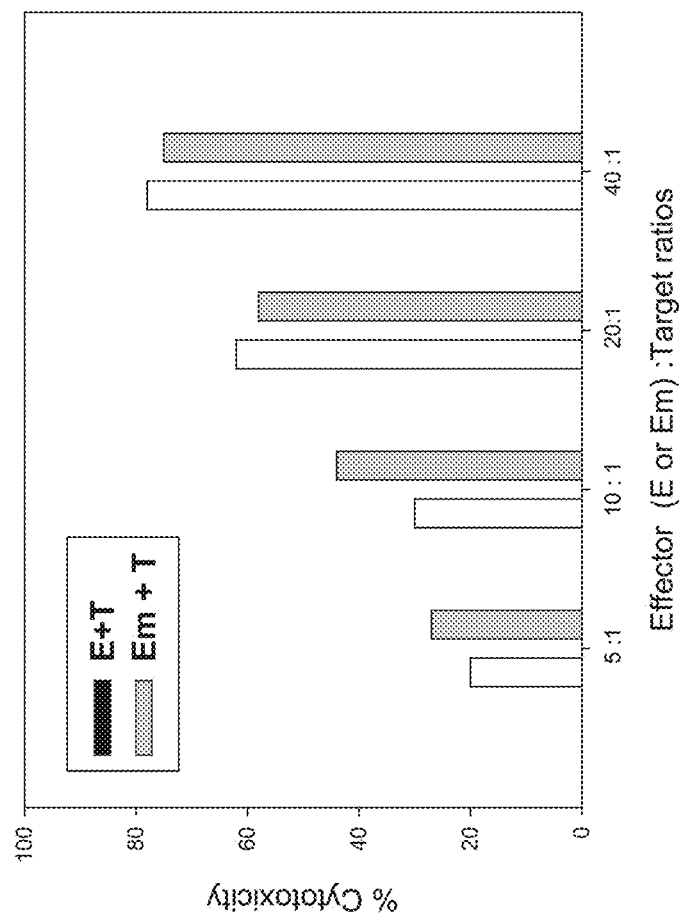
FIG. 22 shows data suggesting genetically engineered γδ T cells retained their cytotoxicities towards GBM cells. E is Wild type γδ T cells; Em is gene-modified γδ T cells T is SB19 (GBM) cell lines; (four-hour cytotoxicity assay).
Figure 23:
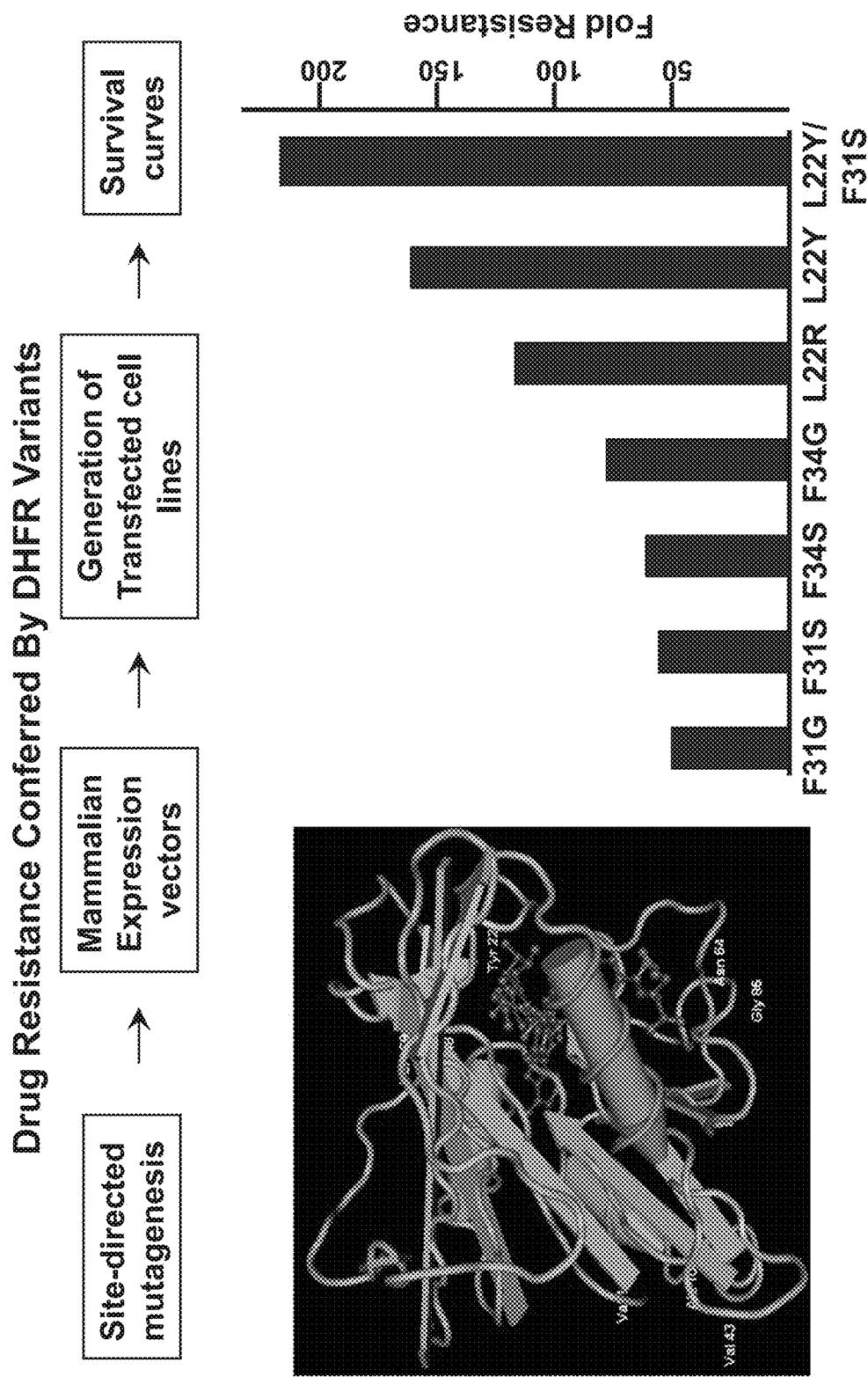
FIG. 23 shows a molecular model of DHFR and the locations of variant sites. Also shown is a graph showing the effectiveness of the variants in conferring drug resistance to cells transfected and expressing the variant polypeptides.
Figure 24A:
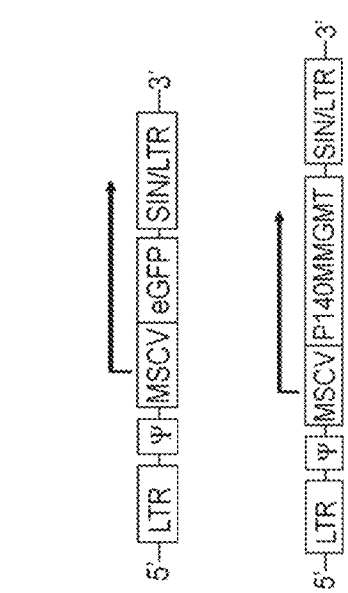
FIGS. 24A-24D are a series of graphs that illustrate the determination of transduction efficiencies for immunocompetent and experimental target cells.
Figure 24B:
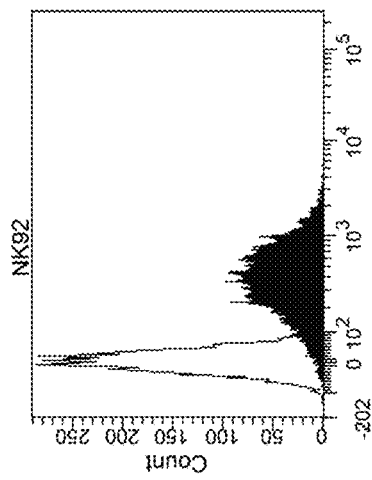
Figure 24D:
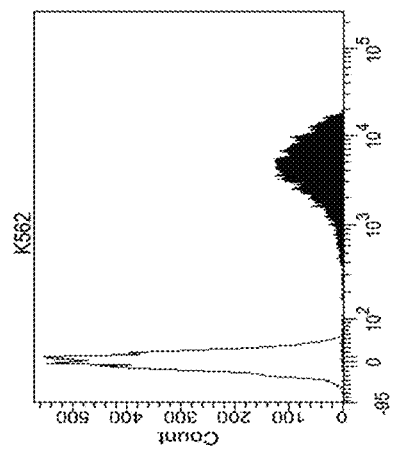
Figure 24C:
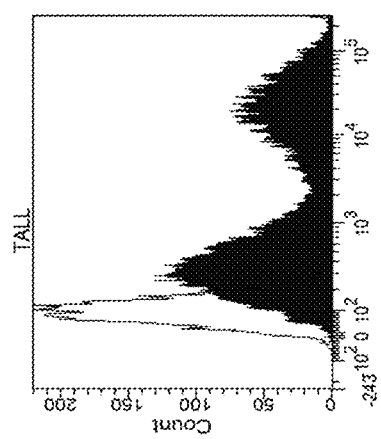

It has also been observed that the reduction in tumors may be transient when a chemotherapeutic agent is used (FIG. 18), and the immunotherapeutic reduction in tumor size may also show a rebound (FIG. 19). In contrast, if the chemotherapeutic agent and the immunotherapy are administered together or sequentially to the subject, then a significant and prolonged reduction in tumor size is seen (FIG. 20). Survival of the subject treated animal is also increased. Transfer of splenocytes from such a successfully treated subject to a subject injected with a cancer cell population resulted in increased survival (FIG. 21) showing the prolongation of cancer-specific cells after curing of a cancer. The experiments, as summarized in FIG. 22, show that application of transduction of a drug-resistance to immune system cells allows for the practical application of a combination of chemotherapy and immunotherapy to increase survival, and destruction of tumors. This method has also been applied to the regression of very large tumors, as shown in FIG. 23.

While treatment protocols for use against cancerous tumors has been of some success, as evidenced by the data presented in FIGS. 15-23, the success of such methods with glioblastomal tumors has been minimal, with prolonged survival of the patient not extending beyond about 24 months. Accordingly, the methods of the present disclosure provide an alternative immunotherapy step that employsisolated cytotoxic immune cells, and particularly the subpopulation of γδ T-cells that can specifically recognize, bind to, and destroy cancer cells that produce the cell-surface stress antigen MICA/B. γδ T-cells comprise only about 5% of the total circulating T-cells and form a powerful component of the innate defense system. In the methods of the disclosure, CD4−CD8− cells may be isolated from T-cell populations by such well known methods as FACS and cultured in vitro to expand the population size.

Accordingly, the methods of the present disclosure provide cytotoxic immune cells, such as γδ T-cells, that are genetically modified to comprise a heterologous nucleic acid that, when expressed in the cells confers upon them resistance to the chemotherapeutic agent. The modified T-cells are then able to survive for sufficient time to effectively destroy most if not all of the target cancer cells.

It has now been shown that animals engrafted with glioblastomal cells have a significantly increased survival time when provided the combined treatment of a chemotherapeutic agent and the appropriate genetically modified agent-resistant γδ T-cells that are resistant to the chemotherapeutic agent, compared to animals that have received only the agent.

Figure 7:
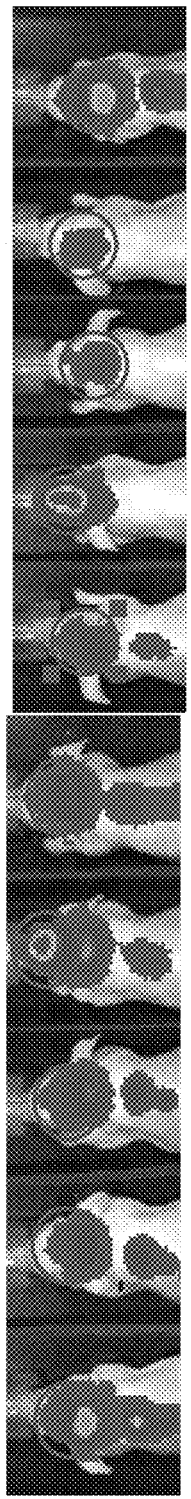
FIG. 7 shows a series of digital images of the development of glioblastomas in mice injected with saline (top) and γδ T-cells (bottom).
Figure 7:
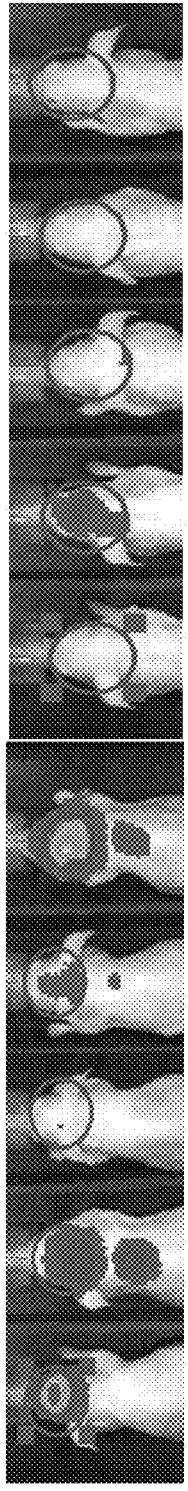
Figure 9:
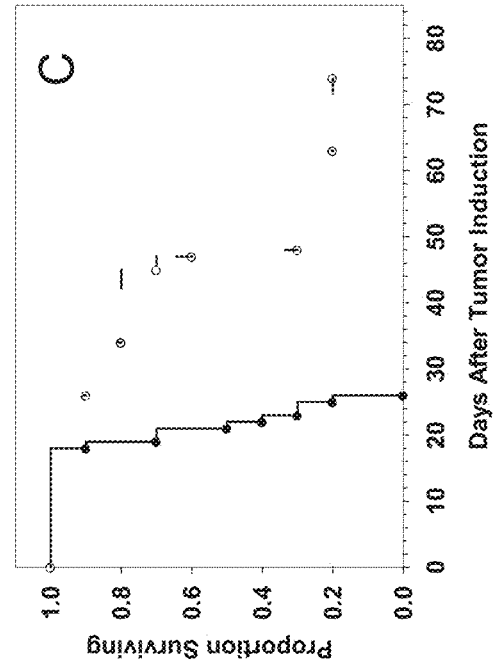
FIG. 9 is a graph showing the increased survival of mice having induced glioblastomas following γδ T-cell treatment (open circles).
Figure 8:
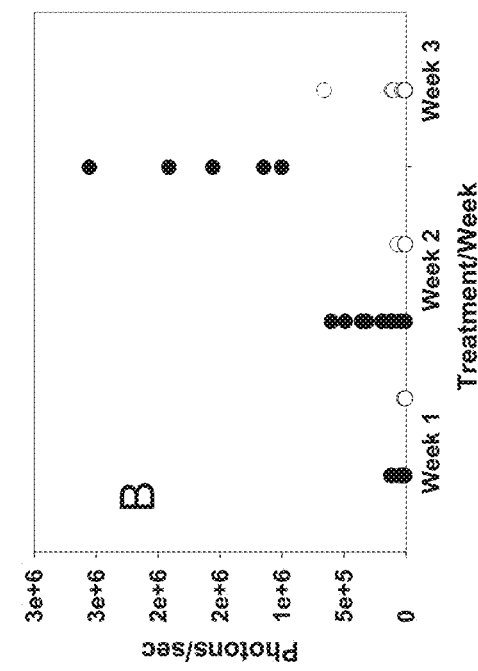
FIG. 8 is a graph showing the imaging density in mice 1-3 weeks after tumor induction and treatment with saline (black circles) or γδ T-cells (open circles).
Figure 10:
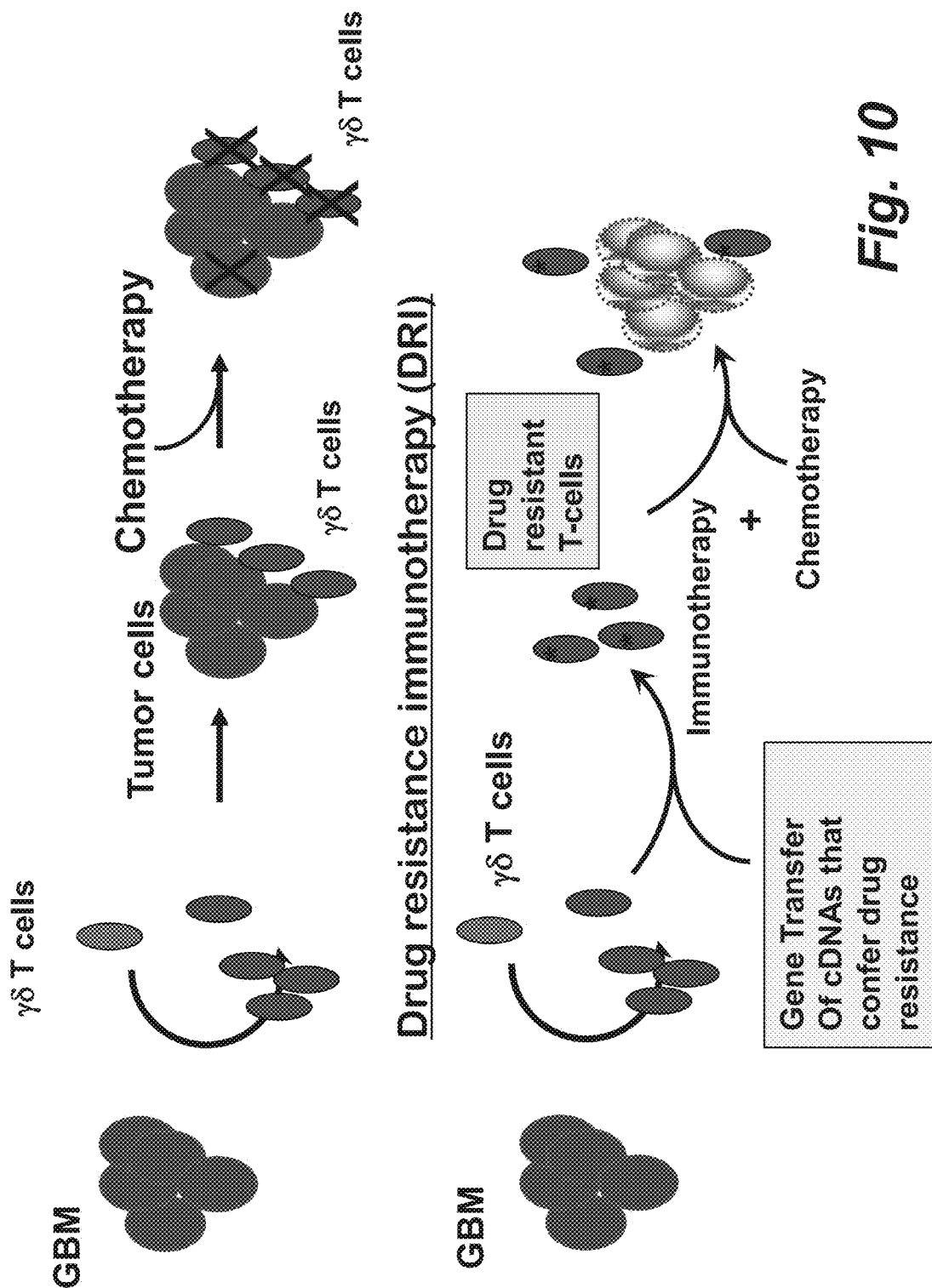
FIG. 10 schematically compares a protocol for combining immunotherapy using γδ T-cells and chemotherapy in the treatment of a cancer, where the γδ immune cells are sensitive (top) and resistant (bottom) to the chemotherapeutic agent.
Figure 12:
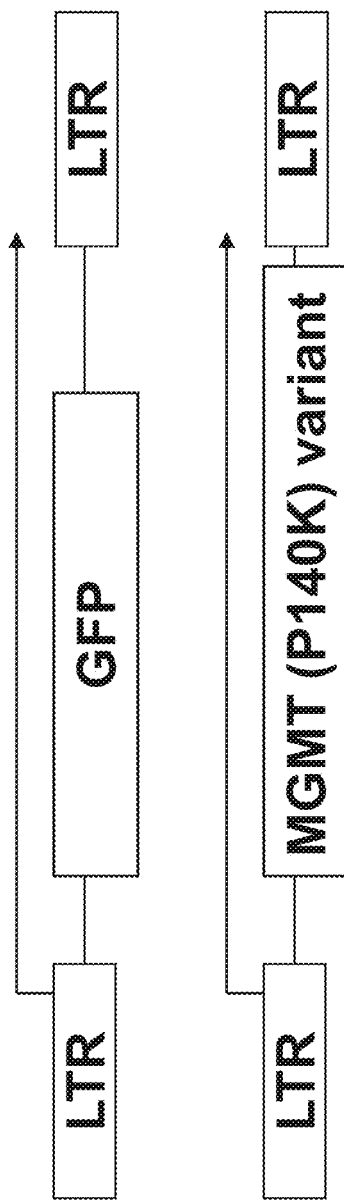
FIG. 12 schematically shows the region of a lentivirus that includes two long terminal repeats (LTR) and a heterologous nucleic acid sequence encoding a green fluorescent protein (GFP) or MGMT variant P104K.
Figure 11:
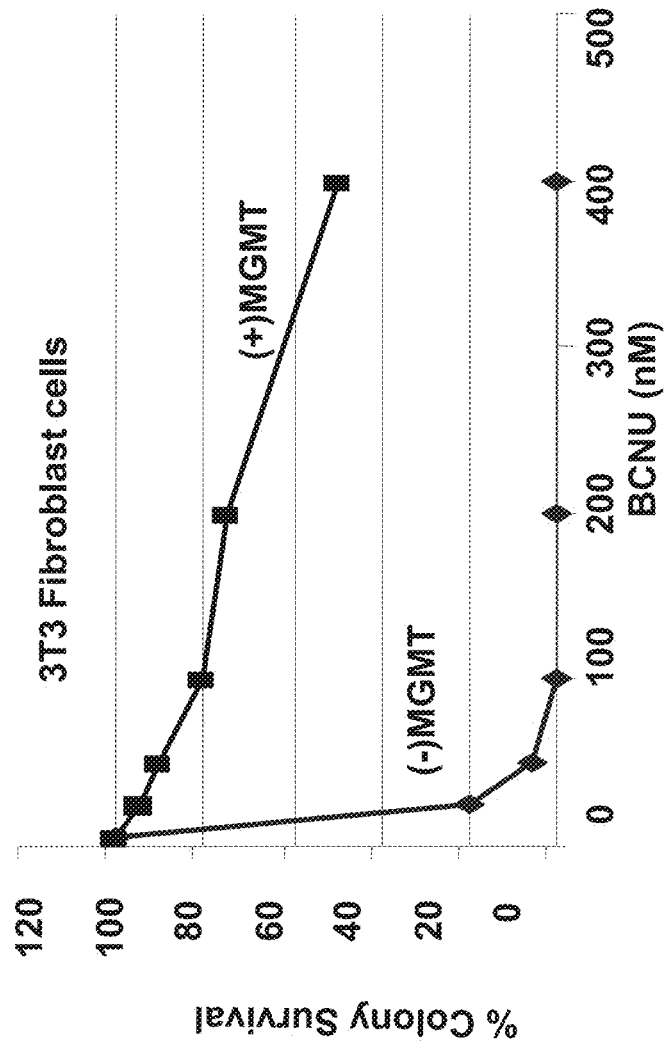
FIG. 11 is a graph illustrating that transduction of fibroblasts with a heterologous nucleic acid sequence encoding MGMT confers resistance to the compound BCNU (bis-chloronitrosourea; CARMUSTINE™), a mustard gas-related α-chloro-nitrosourea compound used as an alkylating agent in chemotherapy, particularly for treatment of glioblastomas.

Genetic modification of the isolated cytotoxic immune cells may be by any method known in the art. For example, but not intended to be limiting, isolated γδ T-cells may be transfected with a lentiviral vector such as SIV comprising a heterologous nucleic acid sequence encoding a variant of the protein MGMT (e.g. a P104K variant). Efficiency of transduction may be shown by co-transfecting the cells with a lentivirus vector comprising a nucleic acid sequence encoding a reporter protein such as, but not limited to, enhanced green fluorescent protein (EGFP) or the like. Transfer of MGMT to cells confers on them resistance to DNA alkylating agents, as shown, for example, in FIG. 7. Similarly, using a recombinant SIV lentivirus vector, γδ T-cells may be transfected with such as MGMT, as shown in FIG. 8.

One aspect of the present disclosure, therefore, encompasses methods for reducing a cancer in a patient, comprising the steps of: obtaining a population of isolated cytotoxic immune cells, where the isolated cytotoxic immune cells have been genetically modified to be resistant to a therapeutic agent; administering to a patient in need thereof, an effective amount of the therapeutic agent; and administering to the patient population of isolated genetically modified cytotoxic immune cells, whereupon the cytotoxic immune cells are delivered to the tumor, thereby reducing the cancer in the patient.

In embodiments of this aspect of the disclosure, the isolated cytotoxic immune cells can be γδ T-cells.

In embodiments of this aspect of the disclosure, the isolated cytotoxic immune cells can be isolated from the patient having the cancer.

In some embodiments of this aspect of the disclosure, the isolated cytotoxic immune cells may be isolated from a source other than the patient in need thereof.

In embodiments of this aspect of the disclosure, the therapeutic agent can have the characteristic of inducing a stress protein in a cancer cell of the patient, where the stress protein is recognized by the cytotoxic immune cells.

In embodiments of this aspect of the disclosure, the therapeutic agent can be a cytotoxic chemotherapeutic agent characterized by a cell developing resistance to said therapeutic agent when the cell receives a heterologous nucleic acid, and wherein the heterologous nucleic acid is expressed in the cell.

In the embodiments of this aspect of the disclosure, the therapeutic agent can be a cytotoxic chemotherapeutic agent selected from the group consisting of: an alkylating agent, a metabolic antagonist, an antitumor antibiotic, and a plant-derived antitumor agent.

In some embodiments of this aspect of the disclosure, the therapeutic agent can be a cytotoxic chemotherapeutic agent selected from the group consisting of: a cyclophosphamide, an ifosamide, a methotrexate, a substituted nucleotide, a substituted nucleoside, fluorouracil, a mitomycin, adriamycin, vincristine, vindesine, Taxol, cisplatin, carboplatin, and etoposide.

In embodiments of this aspect of the disclosure, the therapeutic agent can be selected from the group consisting of: trimethotrixate (TMTX), methotrixate (MTX), temozolomide, raltitrexed, S-(4-Nitrobenzyl)-6-thioinosine (NBMPR), camptothecin, 6-benzylguanidine, and a therapeutic derivative of any thereof.

In embodiments of this aspect of the disclosure, the step of obtaining a population of isolated cytotoxic immune cells genetically modified to be resistant to a therapeutic agent can comprise: isolating from a subject human or animal a population of cytotoxic immune cells; culturing the isolated population of cytotoxic immune cells, thereby increasing the population of the cells; stably transfecting the population of cytotoxic immune cells with a vector comprising a heterologous nucleic acid sequence operably linked to a promoter, wherein the heterologous nucleic acid sequence encodes a polypeptide conferring to the cell resistance to the therapeutic agent.

In embodiments of this aspect of the disclosure, the population of stably transfected cytotoxic immune cells can be viably maintained.

In some embodiments of this aspect of the disclosure, the therapeutic agent can be trimethotrixate or methotrexate, and the heterologous nucleic acid sequence encodes dihydrofolate reductase, or a derivative thereof.

In other embodiments of this aspect of the disclosure, the therapeutic agent can be temozolomide, or a therapeutically agent derivative thereof, and the heterologous nucleic acid sequence may encode $O^6$ methylguanine DNA methyltransferase, or a derivative thereof.

In embodiments of this aspect of the disclosure, the isolated genetically modified cytotoxic immune cells and the therapeutic agent can be co-administered to the patient.

In some embodiments of this aspect of the disclosure, the genetically modified cytotoxic immune cells and the therapeutic agent can be sequentially administered to the patient.

In embodiments of this aspect of the disclosure, the genetically modified cytotoxic immune cells are administered to the patient directly into the tumor or to a blood vessel proximal and leading into the tumor.

In some embodiments of this aspect of the disclosure, the tumor is a glioblastoma.

Yet another aspect of the present disclosure provides systems for treating a cancer in a patient comprising a cytotoxic therapeutic agent having the characteristics of inhibiting the survival of a cancer cell, and an isolated population of cytotoxic immune cells, where the cytotoxic immune cells genetically modified to be resistant to the therapeutic agent.

In embodiments of this aspect of the disclosure, the cytotoxic immune cells can be γδ T-cells.

In embodiments of this aspect of the disclosure, the population of cytotoxic immune cells may comprise a heterologous nucleic acid sequence operably linked to a promoter, where the heterologous nucleic acid sequence encodes a polypeptide that when expressed in a cell confers resistance to the therapeutic agent to the cell.

In embodiments of this aspect of the disclosure, the therapeutic agent is a cytotoxic chemotherapeutic agent selected from the group consisting of: an alkylating agent, a metabolic antagonist, an antitumor antibiotic, and a plant-derived antitumor agent.

In some embodiments of this aspect of the disclosure, the therapeutic agent is selected from the group consisting of: trimethotrixate (TMTX), methotrixate (MTX), temozolomide, reltritrexed, S-(4-Nitrobenzyl)-6-thioinosine (NBMPR), camptothecin, 6-benzylguanidine, and a therapeutic derivative of any thereof.

In certain embodiments of this aspect of the disclosure, the therapeutic agent is trimethotrixate or methotrixate, and the heterologous nucleic acid sequence encodes dihydrofolate reductase, or a derivative thereof.

In some embodiments of this aspect of the disclosure, the therapeutic agent is temozolomide, or a therapeutically agent derivative thereof, and the heterologous nucleic acid sequence encodes $O^6$ methylguanine DNA methyltransferase (MGMT), or a derivative thereof.

Still another aspect of the disclosure provides systems for treating a glioblastoma in a patient comprising a therapeutic agent having the characteristics of inhibiting the survival of a cancer cell and inducing a stress protein in the cancer cell, and an isolated population of cytotoxic immune cells, wherein said cytotoxic immune cells are γδ T-cells, and wherein said γδ T-cells have been genetically modified to be resistant to the therapeutic agent.

In embodiments of this aspect of the disclosure, the population of γδ T-cells comprises a heterologous nucleic acid sequence operably linked to a promoter, wherein the heterologous nucleic acid sequence encodes a polypeptide that when expressed in a cell confers resistance to the therapeutic agent to the cell.

In embodiments of this aspect of the disclosure, the therapeutic agent is a cytotoxic chemotherapeutic agent selected from the group consisting of: an alkylating agent, a metabolic antagonist, an antitumor antibiotic, and a plant-derived antitumor agent.

In some embodiments of this aspect of the disclosure, the therapeutic agent is selected from the group consisting of: trimethotrixate (TMTX), methotrixate (MTX), temozolomide, reltritrexed, S-(4-Nitrobenzyl)-6-thioinosine (NBMPR), camptothecin, 6-benzylguanidine, and a therapeutic derivative of any thereof.

In some embodiments of this aspect of the disclosure, the therapeutic agent is trimethotrixate or methotrixate, and the heterologous nucleic acid sequence encodes dihydrofolate reductase, or a derivative thereof.

In other embodiments of this aspect of the disclosure, the therapeutic agent is temozolomide, or a therapeutically agent derivative thereof, and the heterologous nucleic acid sequence encodes $O^6$ methylguanine DNA methyltransferase (MGMT), or a derivative thereof.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

EXAMPLES

Example 1

Generation and Titering of Recombinant Retrovirus:

The cDNAs encoding for human P140KMGMT and eGFP were PCR amplified using appropriate primers (such as, for example, for: MGMT: Forward: AAACTG-GAGCTGTCTGGCTGTGAA (SEQ ID NO: 1), Reverse: AAACTCTCCTGCTGGAACACTGGA (SEQ ID NO: 2); and DHFR: Forward: CATGGGAAT-TGGCAAGAATGGCGA (SEQ ID NO: 3), Reverse: TGACCAGGTTCTGTTTCCCTTCCA (SEQ ID NO: 4)) and inserted into the appropriate expression vector. The sequences, codon optimized for expression in mammalian cells, encoding MGMT and DHFR, are presented in FIG. 28.

A four plasmid system was used to generate recombinant SIV-lentivirus. Transient transduction was carried out in 293T producer cells using methods as detailed before (Cesano et al., (1998) Anticancer Res. 18: 2289-2295, incorporated herein by reference in its entirety). The titers of virus encoding eGFP and P140KMGMT were determined by flow cytometry and real-time polymerase chain reaction (PCR) methods respectively (Cesano et al., (1998) Anticancer Res. 18: 2289-2295; McMillin et al, (2006) Hum. Gene Ther. 17: 798-806, incorporated herein by reference in their entireties).

Example 2

Lentiviral Transduction:

Transductions of SIV based lentiviral particles were performed by incubating cells with virus in media supplemented with polybrene (8 mg/ml; Specialty Media, Phillipsburg, NJ). Twenty-four hours post transduction, virus-containing medium was replaced with fresh medium and transduced cells were cultured until reaching approximately 70-90% confluency at which point cells were used for downstream applications.

Figure 25A:
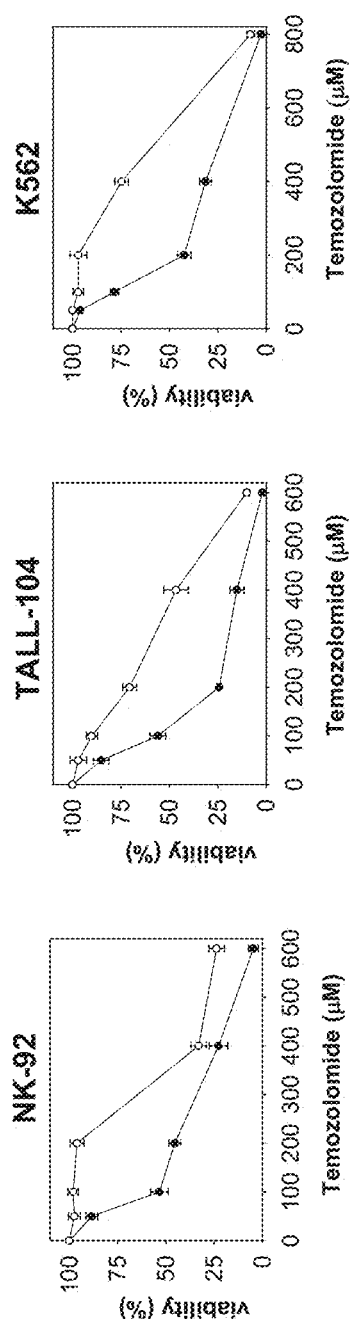
FIG. 25A is a series of graphs showing the survival curve analyses of P140KMGMT-modified (open circles) and non-modified (closed circles) NK-92 cells (left panel), TALL-104 cells (middle panel) and K562 cells (right panel) cells after 6-BG/TMZ treatment. The cells were treated with 25 µM 6-BG and increasing concentrations of TMZ. Forty eight hours later, cell viabilities were measured by a trypan blue method. Each data point in all the graphs represents the mean of triplicate values.

Lentiviral Transduction Efficiencies of NK-92, TALL-104 and K562 Cells:

NK-92, TALL-104 and K562 cells were initially evaluated for their transduction efficiency using a self-inactivating (SIN) recombinant SIV lentivirus, pseudo typed with the VSV-G envelope protein, encoding eGFP, the constructs of which are schematically shown in FIG. 25A.

Figure 25B:
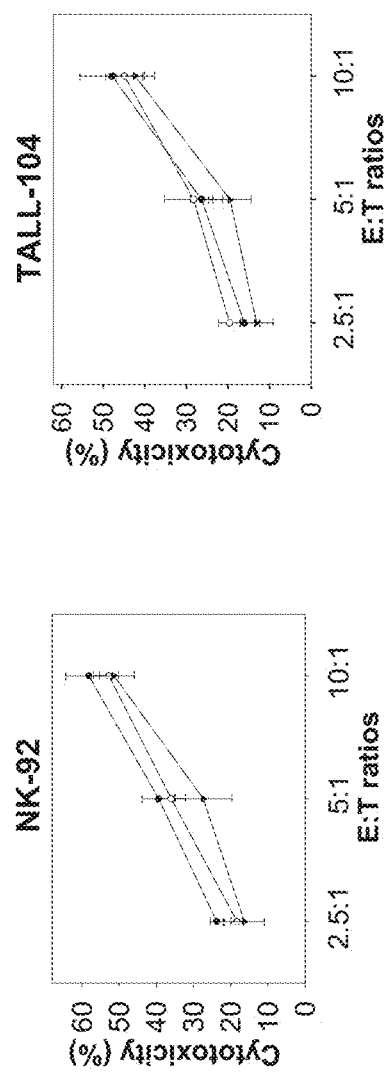
FIG. 25B is a pair of graphs showing the cytotoxic activities of the immune effector NK-92 cells (left panel) and TALL-104 cells (right panel) against K562 target cells at different effector:target (E:T) cell ratios. Different concentrations of P140KMGMT-modified cells (open circles), gene-modified cells after selection with 25 µM 6-BG/200 µM TMZ (reverse triangle), or non-modified cells (closed circles) were mixed with a fixed concentration of the target cells and LDH release assays were performed after 4 hours. Each data point in all the graphs represents the mean of triplicate values.

The expression of eGFP in the lentiviral reporter construct was driven by the murine stem cell virus promoter. To measure the transduction efficiencies, all cell lines were inoculated with an MOI of 40 and GFP fluorescence was analyzed by flow cytometry at 72 hrs after transduction. Transduction of each cell line resulted in robust expressions of eGFP (as visualized by fluorescence microscopy) that were quantitated as 90%, 41% and 99% in the NK-92, TALL-104 and K562 cell lines, respectively, as shown in FIGS. 25B-25D. Thus, high transduction efficiencies are achieved for both the NK-92 and K562 cell lines, and the TALL-104 cell line exhibited moderate transduction efficiency.

Example 3

Survival Curve Analysis:

The non-modified and P104KMGMT modified cells were exposed 2 hours to 6-BG (25 µM) followed by exposure to increasing concentrations of TMZ for 48 hrs. Cell viability was then accessed by a standard trypan blue exclusion method. All drugs were freshly prepared on the day of drug treatment.

To determine the effectiveness of drug resistant P140KMGMT, transduced and untransduced immunocompetent cells were incubated with 6-BG for 2 hrs. TMZ was added at increasing concentrations, and the cells were incubated for 48 hrs. Survival curves were generated with respect to the non-transduced cells.

Figure 26:
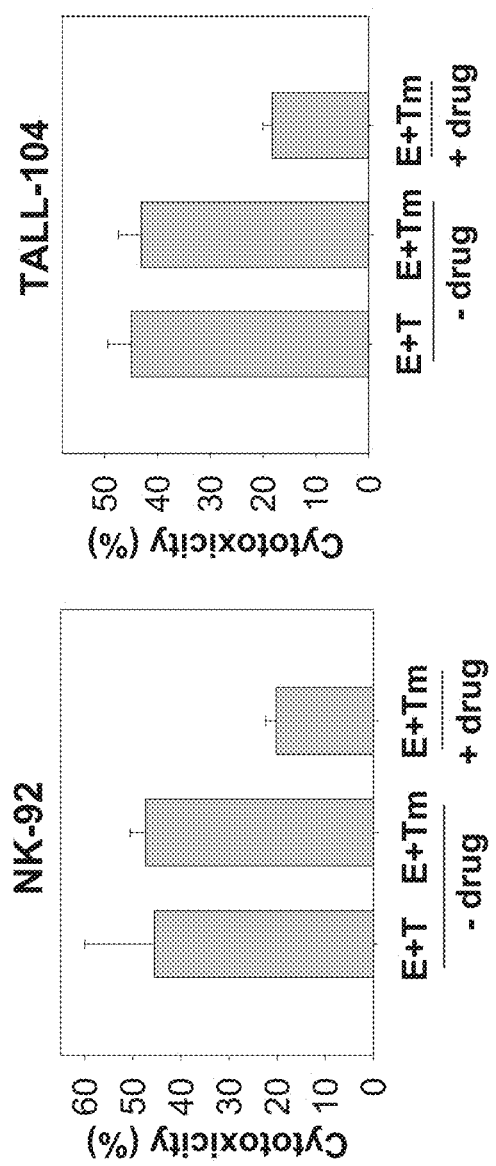
FIG. 26 is a pair of graphs showing non-engineered immune effector cell-mediated lysis of the target K562 cells. Non-modified (E) effector cells, and non-modified (T) or gene-modified (Tm) target K562 cells were treated with 25 µM 6-BG/200 µM TMZ overnight. The non-modified (E) effector cells were then mixed with either non-modified (T) or gene-modified (Tm) target K562 cells at an E:T ratio of 10:1. The cytotoxic activities of the effector cells were then measured. Panel A represents NK-92 cell-mediated lysis; Panel B represents TALL-104 cell-mediated lysis.
Figure 27A:
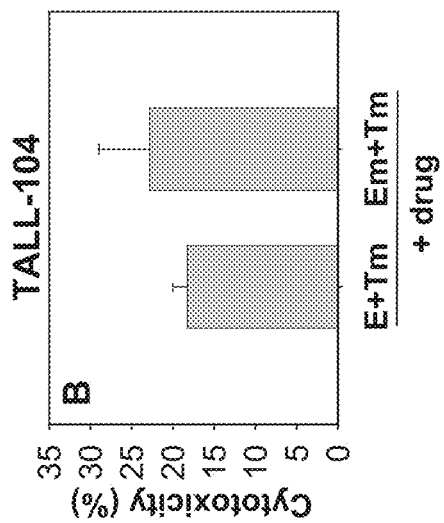
FIGS. 27A-27D are a series of graphs illustrating genetically engineered immune effector cell mediated lysis of the target K562 cells in the presence of 6-BG/TMZ. The non-modified (E) and gene-modified (Em) effector cells, and the non-modified (T) or gene-modified (Tm) target cells were treated with 25 µM 6-BG/200 µM TMZ overnight. The non-modified or modified effector cells were incubated with gene-modified target cells at an E:T ratio of 10:1, and cytotoxic activities of the effector cells were measured. Different combinations of either non-modified or gene-modified effector cells were mixed with either non-modified or gene-modified target cells at an E:T ratio of 10:1. Cytotoxicities of the effector cells were determined.
Figure 27B:
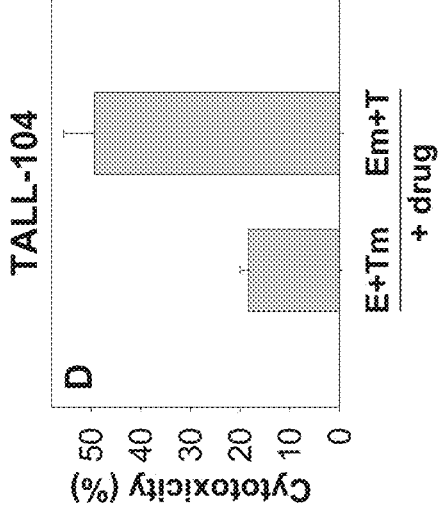
Figure 27C:
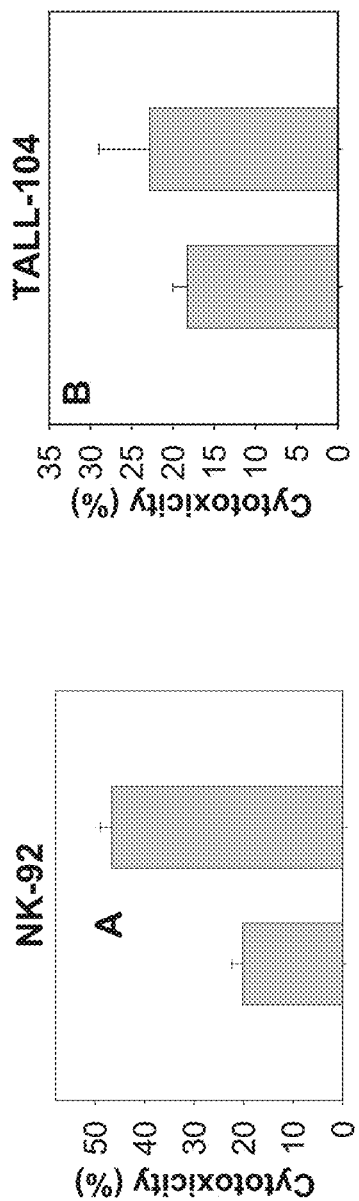
Figure 27D:
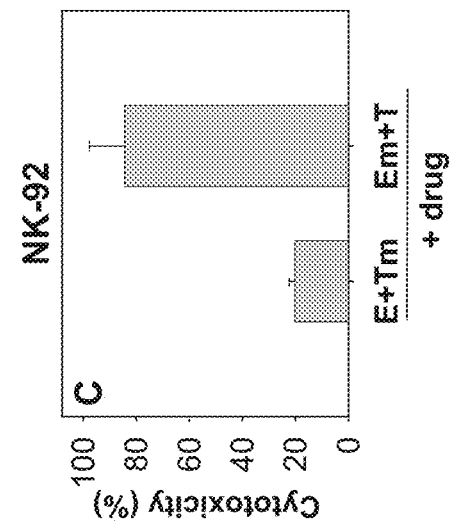

P140KMGMT transduced NK-92, TALL-104 and K562 cells were resistant to the 6-BG/TMZ combination when compared to untransduced control cells, as shown in FIG. 26). Such resistance was pronounced up to 200 µM TMZ, at which point nearly all modified cells survived the drug challenge.

The degrees of resistance achieved by genetic modification of each of the cell lines were measured by calculating the TMZ $IC_{50}$ value. The $IC_{50}$ of 6-BG/TMZ based on 48 hrs exposure were 360±8 µM and 135±4 µM, respectively, in the gene-modified and unmodified NK-92 cells; 385±5 µM and 120±6 µM, respectively, in the gene-modified and unmodified TALL-104 cells; and 550±8 µM and 170±10 µM, respectively, in the gene-modified and unmodified K562 cells. Each of the cell lines, therefore, showed approximately a three-fold resistance to TMZ in a 48 hr viability assay. Similar resistance levels have been achieved in hematopoietic stem cells and K562 cells, but using a 7-10 day survival assay (Gangadharan et al., (2006) Blood. 107: 3859-3864). The choice of the present 48 hr assay period was based on downstream processing cytotoxic assays.

Example 4

Cytotoxicity Assay:

The cells, grown in the presence of 100 U/mL recombinant human IL-2, were exposed to 25 µM 6-BG for 2 hrs followed by the addition of 200 µM☐TMZ and incubating them overnight. To determine the effector cell concentration that resulted in maximal killing of the target cells, 4,000 (T) cells were placed in 96-well plates and mixed with the effector (E) cells (NK-92 or TALL-104) at E:T ratios of 2.5:1, 5:1, and 10:1 (in triplicate) followed by a 4 hrs incubation. The amount of LDH released to the supernatant as a result of cytolysis of target cells were measured in a lactate dehydrogenase (LDH) release assay (Roche Applied Science, Indianapolis, IN). Cytotoxicities were expressed as % cytotoxic activity of the effector cells according to the following formula:

$$\% \text{ cytotoxicity} = \frac{(\text{Experimental release} - \text{Spontaneous release}_{effector}) - \text{Spontaneous release}_{target}}{\text{Mamimum release}_{target} - \text{Spontaneous release}_{target}} \times 100$$

To determine the effectiveness of the genetic modifications had on the cytotoxicities of the effector cells, the non-modified/gene-modified effectors (E/Em) and target (T/Tm) cells were exposed to 6-BG/TMZ for 24 hrs and cytotoxic assays were performed as detailed above.

Drug Resistant Variants of NK-92 and TALL-104 Cell Lines Mediate Effective Target Cell Killing:

It has been reported that the NK-92 and TALL-104 cell lines can efficiently lyse the leukemic K562 cell line. In the present example, it was determined if genetic modification of these immune effector cell lines resulted in a change in their cytotoxic abilities towards the target cell line K562. Accordingly, gene-modified and non-modified effector cells were mixed with a fixed number of the target cells at various effector:target ratios of 2.5:1, 5:1 and 10:1 Killing effectiveness of each of the drug resistant effector cells were compared with the unmodified control cells in a 4 hour cytotoxicity assay. When compared to the non-modified cells, both the gene-modified drug resistant immune effector cells, NK-92 and TALL-104 cells showed similar cytolytic activities toward the target cell line, as shown in FIG. 2B, thereby establishing that the genetic modifications imparted to the NK-92 and TALL-104 transduced cell lines did not appear to affect cytotoxicity properties of the cells.

Retention of Cytotoxic Effectiveness of Gene-Modified Immunocompetent Cells after Expansion in the Presence of 200 µM TMZ.

As shown in FIG. 2B, the cytotoxicities of the drug selected gene-modified effector cell lines NK-92 and TALL1-04, were similar to the cytotoxicities of the non-selected gene-modified effector cells. These results show that the drug resistant immunocompetent cell lines, after modification with P140KMGMT, retained their ability to efficiently lyze target cells.

Example 5

Generation of Drug Resistant Effector and Target Cell Lines by Lentiviral Transduction:

The P140KMGMT cDNA sequence was inserted into the SIV expression vector by replacing the sequence encoding eGFP (as shown in FIG. 25A). Virus titers, determined using 293T cells as targets, were $10^7$-$10^8$ TU/ml. Gene transfer into effector and target cells was quantitated by real-time PCR amplification using genomic DNA isolated from cells transduced with the recombinant virus at an MOI of 40.

P140KMGMT copy numbers for the transduced NK-92, TALL-104 and K562 cells were determined to be 3±0.28, 1±0.14, and 4±0.41, respectively. MGMT mRNA levels were also measured in K562 cells to confirm that gene-modified cells express increased levels of MGMT message. MGMT mRNA expression was readily detected in the transduced K562 cells, while MGMT mRNA expression levels in untransduced K562 cells was below the linear range of detection. Previous studies (Gangadharan et al., (2006) Blood. 107: 3859-3864) also reported extremely low MGMT protein levels in wild-type K562 cells.

We claim:

1. A composition comprising a carrier and isolated natural killer (NK) cells, wherein greater than about 50% of the NK cells express a heterologous polypeptide that confers resistance to a chemotherapy agent, and wherein the NK cells that express the heterologous polypeptide are present in a therapeutically effective amount.

2. The composition of claim 1, wherein the heterologous polypeptide that confers resistance to a chemotherapy agent is O6-methylguanine DNA methyltransferase (MGMT), a drug resistant variant of dihydrofolate reductase (L22Y-DHFR), thymidylate synthase, or multiple drug resistance-1 protein (MDRI).

3. The composition of claim 1, wherein the heterologous polypeptide that confers resistance to the chemotherapy agent is O6-methylguanine DNA methyltransferase (MGMT).

4. The composition of claim 1, wherein the chemotherapy agent induces production of a stress protein in a cancer cell of a patient, and wherein the stress protein is recognized by the NK cells.

5. The composition of claim 1, wherein the composition is formulated for injection into a patient.

6. The composition of claim 1, wherein the chemotherapy agent is temozolomide and the heterologous polypeptide conferring resistance to the chemotherapy agent is O6-methylguanine DNA methyltransferase (MGMT).

7. The composition of claim 1, wherein the heterologous polypeptide that confers resistance to a chemotherapy agent is thymidylate synthase or multiple drug resistance-I protein (MDRI).

8. A composition comprising a carrier and isolated NK cells wherein greater than about 50% of the NK cells comprise a nucleic acid that encodes a heterologous polypeptide, wherein upon expression of the heterologous polypeptide by the NK cell, the heterologous polypeptide confers resistance to a chemotherapy agent, and wherein the NK cells that comprise the nucleic acid that encodes the heterologous polypeptide are present in a therapeutically effective amount.

9. The composition of claim 8, wherein the heterologous polypeptide that confers resistance to a chemotherapy agent is O6-methylguanine DNA methyltransferase (MGMT), a drug resistant variant of dihydrofolate reductase (L22Y-DHFR), thymidylate synthase, or multiple drug resistance-1 protein (MDRI).

10. The composition of claim 9, wherein the heterologous polypeptide that confers resistance to a chemotherapy the chemotherapy agent is O6-methylguanine DNA methyltransferase (MGMT).

11. The composition of claim 8, wherein the chemotherapy agent induces production of a stress protein in a cancer cell of a patient, and wherein the stress protein is recognized by the NK cells.

12. The composition of claim 8, wherein the composition is formulated for injection into a patient.

13. The composition of claim 9, wherein the chemotherapy agent is temozolomide and the heterologous polypeptide conferring resistance to the chemotherapy agent is O6-methylguanine DNA methyltransferase (MGMT).

14. The composition of claim 9, wherein the heterologous polypeptide that confers resistance to a chemotherapy agent is thymidylate synthase or multiple drug resistance-I protein (MDRI).

* * * * *